(12) United States Patent
Moro et al.

(10) Patent No.: US 11,564,883 B2
(45) Date of Patent: Jan. 31, 2023

(54) ORAL RIFAMYCIN SV COMPOSITIONS

(71) Applicant: COSMO TECHNOLOGIES LTD., Dublin (IE)

(72) Inventors: Luigi Moro, Lainate (IT); Luigi Maria Longo, Lainate (IT)

(73) Assignee: COSMO TECHNOLOGIES LTD., Dublin (IE)

( * ) Notice: Subject to any disclaimer, the term of this patent is extended or adjusted under 35 U.S.C. 154(b) by 9 days.

(21) Appl. No.: 16/762,760

(22) PCT Filed: Nov. 7, 2018

(86) PCT No.: PCT/IB2018/058748
§ 371 (c)(1),
(2) Date: May 8, 2020

(87) PCT Pub. No.: WO2019/092614
PCT Pub. Date: May 16, 2019

(65) Prior Publication Data
US 2020/0281850 A1  Sep. 10, 2020

Related U.S. Application Data

(60) Provisional application No. 62/584,226, filed on Nov. 10, 2017.

(51) Int. Cl.
*A61K 31/395* (2006.01)
*A61K 9/28* (2006.01)
(Continued)

(52) U.S. Cl.
CPC .......... *A61K 9/0053* (2013.01); *A61K 9/2846* (2013.01); *A61K 31/395* (2013.01); *A61P 1/12* (2018.01)

(58) Field of Classification Search
None
See application file for complete search history.

(56) References Cited

U.S. PATENT DOCUMENTS 8,263,120 B2  9/2012  Ajani et al.
8,486,446 B2  7/2013  Ajani et al.
(Continued)

FOREIGN PATENT DOCUMENTS

CN  101317826 A  12/2008
CN  101351206 A  1/2009
(Continued)

OTHER PUBLICATIONS

International Preliminary Report on Patentability, issued in corresponding International Application No. PCT/IB2018/058748, dated May 22, 2020, 7 pages.
(Continued)

Primary Examiner — Lakshmi S Channavajjala
(74) Attorney, Agent, or Firm — Rothwell, Figg, Ernst & Manbeck, P.C.

(57) ABSTRACT

Oral pharmaceutical compositions containing rifamycin SV, or a pharmaceutically salt thereof, characterized in that they are formulated in a higher strength (about 600 mg/tablet) and in such a manner to obtain a modified profile of the rifamycin SV, or a pharmaceutically acceptable salt thereof, in the proximal portion of the intestine, i.e. in the small intestine (duodenum, jejunum and ileum). In one embodiment, the disclosed oral pharmaceutical compositions are used in the prevention and/or treatment in a subject of small intestine bacterial overgrowth (SIBO) and/or irritable bowel syndrome (IBS) and/or in the treatment of cholera. In one embodiment, the disclosed oral pharmaceutical compositions are used in the prevention and/or treatment in a subject of hepatic encephalopathy, hepatic cirrhosis, pouchitis and/or spontaneous bacterial perotinitis. In one embodiment, the (Continued)

disclosed oral pharmaceutical compositions are used in the prevention and/or treatment in a subject of non-alcoholic fatty liver disease, non-alcoholic fatty liver or non-alcoholic steatohepatitis.

18 Claims, 3 Drawing Sheets

(51) Int. Cl.
*A61P 1/00* (2006.01)
*A61K 9/00* (2006.01)
*A61P 1/12* (2006.01)

(56) References Cited

U.S. PATENT DOCUMENTS

| | | |
|---|---|---|
| 8,529,945 B2 | 9/2013 | Ajani et al. |
| 8,741,048 B2 | 6/2014 | Okuda et al. |
| 8,741,948 B2 * | 6/2014 | Ajani .................... A61K 9/282 514/450 |
| 9,532,954 B2 | 1/2017 | Villa et al. |
| 9,949,958 B2 | 4/2018 | Forbes |
| 2008/0233193 A1 | 9/2008 | Aiani et al. |
| 2013/0209559 A1 | 8/2013 | Proehl et al. |
| 2014/0370093 A1 | 12/2014 | Ajani et al. |
| 2015/0017239 A1 | 1/2015 | Moro et al. |
| 2019/0192441 A1 | 6/2019 | Ajani et al. |
| 2020/0163888 A1 | 5/2020 | Proehl et al. |
| 2020/0276170 A1 | 9/2020 | Golden et al. |

FOREIGN PATENT DOCUMENTS

| | | |
|---|---|---|
| CN | 101959412 A | 1/2011 |
| JP | 2003-501457 A | 1/2003 |
| JP | 2008-503540 A | 2/2008 |
| JP | 2012-504649 A | 2/2012 |
| JP | 2015-506999 A | 3/2015 |
| JP | 2017-520624 A | 7/2017 |
| WO | 2005030173 A1 | 4/2005 |
| WO | 2006003043 A1 | 1/2006 |
| WO | 2007/077893 A1 | 7/2007 |
| WO | 2009108814 A1 | 9/2009 |

OTHER PUBLICATIONS

The International Search Report and the Written Opinion issued for International application No. PCT/IB2018/058748, dated Feb. 12, 2019, 8 pages.

Office Action for Russian patent application No. 2020119035 dated Apr. 20, 2022, English translation, 4 pages.

Office Action for European patent application No. 18807426.4 dated Mar. 22, 2022, 3 pages.

Pertsev, Pharmaceutical and biomedical aspects of drugs, T.1, 1999, pp. 253-254 (2 pages), English translation.

"Rifaximin, a drug for diarrhea in tourists," World Notes on Antibiotics, 2005, vol. 26, No. 6, with machine translation, 23 pages.

Clinical Trials, "Rifamycin SV-MMX 600 mg Tablets Administered Three or Two Times Daily to Patients With IBS-D" [online], Mar. 2017 (Search Date: Aug. 25, 2022) <URL:https://clinicaltrials.gov/ct2/history/NCT03099785?A=1&B=1&C=merged#StudyPageTop<, 7 pages.

Di Stefano, A. F. D., et al., "Systemic absorption of Rifamycin SV MMX administered as modified-release tablets in healthy volunteers," Antimicrobial Agents and Chemotherapy, 2011, vol. 55(5):2122-2128.

Lin, S.-W., et al., "Rifamycin SV MMX for the treatment of traveler's diarrhea," Expert Opinion on Pharmacotherapy, Jul. 2017, vol. 18, No. 12, pp. 1269-1277.

Fukudo, Diagnosis and Treatment, 2015, vol. 103, No. 8, pp. 1041-1045 (with concise explanation).

Notice of Rejection in Japanese Patent Application No. 2020-526001 dated Sep. 13, 2022 (English translation), 6 pages.

* cited by examiner

ORAL RIFAMYCIN SV COMPOSITIONS

CROSS REFERENCE TO RELATED APPLICATION(S)

This application is a 35 U.S.C. § 371 National Stage of International Patent Application No. PCT/IB2018/058748, filed Nov. 7, 2018, designating the United States, which claims priority under 35 U.S.C. § 119 to Provisional Patent Application No. 62/584,226, filed Nov. 10, 2017, the disclosures of which are incorporated by reference in their entirety.

BACKGROUND

Intestinal infections are common diseases caused by the colonization of the intestine by foreign pathogenic agents of various origins, or caused by intestinal microorganisms that are normally present becoming virulent.

It is known that the human intestine is divided into two distinct portions:
- the proximal portion, called the "small intestine" or "small bowel," which is formed by three districts known under the name of, in the craniocaudally direction, duodenum, jejunum and ileum, and included between two biologic valves, namely the pylorus and the ileo-caecal valve;
- the distal portion, called the "large intestine" or "large bowel," which is formed by the colon and the rectum-anus (Faller A, Scevola G. *Anatomia e Fisiologia del Corpo Umano (Anatomy and Physiology of the Human Body)*. Vol I. Edizioni Minerva Medica, Turin, 1973, pp. 235-254). This portion of the intestine, in turn, includes several districts known as ascending colon, transverse colon, descending colon, sigmoid colon and rectum.

The two portions, the small intestine and the large intestine, are functionally separated anatomically by the ileocecal valve, which permits the passage of the intestinal contents from the small intestine to the large intestine but, in normal conditions, not vice versa. Besides, from the anatomical-structural point of view, the small intestine is quite different from the large intestine also, and above all, from the functional point of view (Braga P C. Enteric microflora and its regulation. In *Drugs in Gastroenterology*. Raven Press, New York, 1991, pp. 501-508), with the presence of a large absorption surface and a strong peristalsis supported by specific muscular rings in the small bowel and the presence of fenestratum epithelium and evident and regular crypts in the large bowel.

Local environmental factors, such as pH conditions, nutrients and enzyme presence and differentiated transit time for each anatomical region determine which microbial species predominate, as well as determine the bacterial concentration in a particular region. The concentration of bacteria in the small bowel is generally many magnitudes lower than that in the large bowel, due to the microenvironment and anatomical differences between the regions.

These many differences between the small intestine and the large intestine physio-anatomic characteristics explain the distinctive nature of some pathologies which occur at the expense of the small intestine.

It should be noted that diseases of the digestive system have different etiological-pathologies and present various symptoms that allow their diagnosis. The expression "inflammatory bowel disease" or IBD indicates a series of chronic inflammatory intestinal pathologies, including principally ulcerative colitis and Crohn's disease, which should not be confused with "irritable bowel syndrome" or IBS. IBS may be categorized into presenting as IBS-C (constipation predominant) or IBS-D (diarrhea predominant), although mixed symptoms or alternating periods with both symptoms may be present in the same individual in IBS-M (mixed type) presentation, and a fourth category IBS-U (uncategorized) has also been proposed, however the subcategory can vary for an individual over time.

Unlike IBD, IBS does not exhibit obvious anatomical impairment of the mucosa, so that it is considered a predominantly functional disease. From a purely clinical point of view, IBS is characterized by impairment of the intestinal function with abdominal pain, bloating and altered bowel function (diarrhea, constipation, or both). The etiology and the pathogenesis of IBS are not known, but various factors may contribute to causing its onset. Those factors often include anomalies in the regulation of the tone and activity of the smooth musculature of the intestinal wall, the effects of irritant substances of a bacterial nature and psychological and emotional influences. Because the pathophysiology and causes of IBS are poorly understood, treatment approaches to date have mainly focused on symptom management to maintain everyday functioning and improve quality of life of the patient. The mainstay of intervention to date has been pharmacological treatment with antispasmodics and anti-diarrheals for diarrhea, prokinetics and high-fiber diets for constipation, and supportive therapy with low-dose antidepressants to normalize gastrointestinal motility-treatments aimed at alleviating the functional symptoms of the illness. Other interventions including advice on lifestyle and dietary changes and psychological counseling are also used. However, IBS is frequently unresponsive to the current treatment options, including dietary and lifestyle advice, counseling, fiber supplementation, psychological therapy and/or pharmacotherapy.

Recently, it has been reported that the pregnane X receptor (PXR), a ligand-activated nuclear receptor that senses and responds to a variety of chemical stimuli, including intestinal microbial metabolites plays a key role in the intestinal epithelium, regulating inflammatory responses enhancing wound healing and maintaining barrier function under inflammatory conditions (Garg A et al in The Journal of Pharmacology and Experimental Therapeutics, 359:91-101, October 2016). In humans, PXR is most abundantly expressed in the small intestine, colon, liver and gall-bladder and to a lesser extent in the stomach. Activation of PXR induces metabolic enzymes (e.g. CYP3A4), which can impact the pharmacokinetic of xenobiotics and endobiotics. In addition, activating PXR has been shown to attenuate the signaling of nuclear factor-kB (NF-kB), a key transcription factor that regulates gene expression of pro-inflammatory cytokines and chemokines. The distribution and functions of PXR in the GI tract suggest that PXR function may play a role in maintaining mucosal homoeostasis. Thus, activating PXR may potentially contribute to the therapeutic effects in patients with IBS.

Inflammation and immune dysregulation contribute to the pathophysiology of several gastrointestinal (GI) diseases, such as inflammatory bowel diseases (IBD) irritable bowel syndrome (IBS), and diverticular disease. Alterations in the reciprocal crosstalk between two major regulators of inflammation, PXR and NFκB, may play a role in the dysregulation of the inflammatory mechanisms in IBD and IBS.

Constant exposure to xenobiotics is not only capable of producing intestinal inflammation and injury but can also impair immune function. In addition to its role in detoxification mechanisms, PXR has been shown to indirectly inhibit inflammation through repression of NFκB activity. NFκB is the primary transcription factor that regulates gene expression of proinflammatory cytokines and chemokines. Patients with IBD have significantly higher expression of NFκB compared to non-IBD patients. Abnormal activation of NFκB leads to excessive production of pro-inflammatory cytokines that cause chronic inflammation in the bowel, a leading mechanism of IBS.

Small intestinal bacterial overgrowth (SIBO) is a disturbance of the normal GI flora. In SIBO the concentration of bacterial organisms in the terminal jejunum and ileum is increased, and the normal distribution of bacteria is perturbed. In SIBO there is an increased number and/or type of bacteria in the small bowel. A finding of $\leq 10^5$ CFU of bacteria per ml of proximal jejunal aspirate is typical wherein, under normal conditions, the bacterial concentration in the small intestine is not higher than $10^2$ CFU.

According to the current opinion by a person skilled in the art, SIBO can arise as a result of an underlying condition such as pancreatic insufficiency, immunodeficiency syndromes, diverticula, previous surgery, scleroderma, autonomic neuropathy in diabetes, post-radiation enteropathy, or a combination of these factors. Prognosis for patients with SIBO is usually serious and related to the underlying condition. Resulting nutrient malabsorption can result in a variety of symptoms. For example, this change in the distribution and concentration of the normal GI flora in SIBO changes the metabolism of sugar molecules which, as part of a fermentation reaction, are initially broken down into short-chain fatty acids (SCFA), carbon dioxide ($CO_2$) and hydrogen ($H_2$). A large part of the $CO_2$ remains in the intestines and leads to the symptom of bloating. SCFA generate an osmotic gradient and, by doing so, absorb water into the intestinal lumen, which leads to the symptom of diarrhea in IBS.

As a result, there is a significant unmet medical need for more effective treatments for IBS Direct jejunal aspirate measurement and diagnosis of SIBO can lead to false negative results, as it does not include assessment of bacterial overgrowth in other less accessible parts of the distal small intestine. The less invasive hydrogen breath test can provide additional information on the extent of SIBO. Even though prebiotic and probiotic therapies aimed at restoring the natural GI flora have been used empirically for many years by IBS patients, eradication of bacterial overgrowth with antibiotics has been shown to reduce the symptoms of IBS. A range of broad spectrum antibiotics including tetracycline, amoxicillin/clavulanate, metronidazole, and various fluoroquinolones have been used to reduce bacterial overgrowth and treat IBS. However, these compounds frequently have systemic side effects. Moreover, particularly if frequently used, they also could contribute to general resistance to the antibiotics in the bacterial species/strains.

Consequently, there is a significant unmet medical need for more effective and locally limited treatments for SIBO and/or IBS.

Cholera is an acute diarrheal infection caused by ingestion of food or water contaminated with the bacterium *Vibrio cholerae*. Cholera remains a global threat to public health, especially in countries of the Third World or in countries under development: researchers have estimated that every year, there are roughly 1.3 to 4.0 million cases, and 21 000 to 143 000 deaths worldwide (M. Ali et al. Updated Burden of Cholera in Endemic Countries. Negl. Trop. Dis 2015, 9(6)). Cholera can be endemic or epidemic.

Cholera is transmitted by the fecal-oral route. The pathogenic microorganisms are sensitive to acid, and most die in the stomach; those surviving may adhere to and colonize the small bowel, where they secrete the potent cholera enterotoxin (CT, also called "choleragen"). Cholera is an extremely virulent disease that can cause severe acute watery diarrhea that affects both children and adults and can kill within hours if untreated.

Although there are vaccines against cholera, their protection against *V. cholerae* is limited to a few months: (Cholera vaccines: WHO position paper-August 2017. Weekly epidemiological record. 92: 477-500. 25 Aug. 2017). Therefore, vaccine cannot entirely protect against cholera outbreaks in endemic areas. The current treatment of cholera includes a rapid rehydration (either by oral or by intravenous administration) to replace the fluids and electrolytes lost due to the watery diarrhea. In addition, treatment with antibiotics is recommended, in particular for patients who are severely or moderately dehydrated and continue to pass a large volume of stool during rehydration treatment. Antibiotic choices should be informed by local antibiotic susceptibility patterns. In most countries, doxycycline is recommended as first-line treatment for adults, while azithromycin is recommended as first-line treatment for children and pregnant women. Also ampicillin, erythromycin, and fluoroquinolones have been reported as efficacious antibiotics for treatment of cholera. In the last years, however, several reports on multi-drug resistant strains of *V. cholerae* have been published in specialized scientific literature (T. Shrestha et al. BMC Infectious Diseases (2015) 15:104; J Health Popul. Nutr. (2007), 25(2):241-243; M. Kitaoka et al. Journal of Medical Microbiology (2011), 60, 397-407).

Therefore, there is the need for a new antibiotic therapy for cholera, possibly targeted to the GI tract where the *Vibrio cholerae* colonizes the host: this would allow for a local maximum concentration of the antibiotic where it has to act, with a consequent faster eradication of the pathogenic bacteria and a faster resolution of the symptoms.

Currently, the oral therapy of intestinal infections uses substances having antibacterial activity which must have specific characteristics such as: broad spectrum activity on Gram+ and Gram− bacteria, resistance to strongly acidic environments, such as the gastric environment, anti-infectious activity independent of the presence of the intestinal biomass, residence inside the intestine for an appropriate period of time, good penetrability into the infecting host cell and good tolerability (Braga P C. Interaction of antibiotics on enteric microflora. In: *Drugs in Gastroenterology*. Raven Press, New York, 1991, pp. 509-517).

Therapy with antibacterial agents administered in the oral preparations employed today has at least two limitations. In the first place, the antibacterial agents, if not suitably protected, may lose their efficacy owing to the enzymatic or degradative inactivation which occurs during their passage through the stomach.

In addition, the pharmaceutical forms nowadays used, although they permit the administration of the active ingredient in discrete doses, release it too rapidly in relation to the time taken to pass through the digestive tract, so that the active ingredient performs its anti-infectious activity in an indiscriminate manner along the entire gastro-intestinal tract.

In addition, although the antimicrobial agents used for the disinfection of the digestive tract do not often have a high rate of metabolism, in order to maintain unaltered the therapeutic possibility connected with the administration of a traditional form containing antimicrobial agents, no phenomenon of metabolic degradation should occur, in order to avoid any weakening of the therapeutic efficacy associated with the presence of the antimicrobial agent.

Therefore, in such cases, in order to ensure the real efficacy of the anti-infectious therapy in SIBO, IBS or cholera, there is a need for an extended and site-specific form of administration to the small intestine with possible carry over in the large intestine, in adherence to the transit of the bolus inside the digestive tract.

Hepatic Encephalopathy (HE) is a brain disorder that develops in some individuals with liver disease. HE is a complex disorder that encompasses a spectrum or continuum of disease that ranges from a subtle condition with no outward signs or symptoms to a severe form that can cause serious, life-threatening complications. Symptoms are related to progressive dysfunction of the brain and may include personality changes, intellectual impairment, impaired memory and loss of consciousness (coma). HE can occur in individuals with acute or chronic liver (hepatic) disease or in individuals whose liver is bypassed by a portosystemic shunt (with no liver disease present). A portosystemic shunt is an abnormal passageway that allows blood from the gastrointestinal tract to bypass the liver. They can be present at birth (congenital) or acquired during life. HE is caused when toxins that are normally cleared from the body by the liver accumulate in the blood, eventually traveling to the brain. Many of the symptoms of hepatic encephalopathy are reversible when promptly detected and treated. The exact pathogenesis of HE is not completely understood. It is theorized that neurotoxic substances, including ammonia and manganese, may gain entry into the brain in the setting of liver failure. In particular, ammonia is produced in the gastrointestinal tract by degradation of amines, amino acids, purines, and urea by bacterial microflora. Normally, the produced ammonia is detoxified in the liver by conversion to urea by the Krebs-Henseleit cycle. Ammonia is also consumed in the conversion of glutamate to glutamine, a reaction that depends upon the activity of glutamine synthetase. Two factors contribute to the hyperammonemia that is seen in HE in cirrhotic patients. First, there is a decrease in the mass of functioning hepatocytes, resulting in fewer opportunities for ammonia to be detoxified by the above processes. Secondly, portosystemic shunting may divert ammonia-containing blood away from the liver to the systemic circulation.

Initial therapies may be aimed at identifying and removing a triggering event such as infection, gastrointestinal bleeding, certain drugs or kidney dysfunction. Such therapies may include medications to treat infections, medications or procedures to alleviate or control bleeding, stopping the use of medications that can trigger an episode and any appropriate therapy for kidney issues.

Hepatic encephalopathy is a chronically debilitating complication of hepatic cirrhosis. Another complication of hepatic cirrhosis are bacterial infections which are more common in patients with cirrhosis than in the general population, and those with decompensated cirrhosis are more susceptible to infection than those with a compensated lesion. Antibiotics are one course of treatment for such infections. Furthermore, antibiotic prophylaxis is necessary in patients with cirrhosis who have gastrointestinal bleeding.

Patients with IBD, especially Ulcerative Colitis (UC), in whom available medical therapy has failed or serious life-threatening complications have ensued, have to undergo a surgery to remove the colon and rectum (proctocolectomy) to resolve their diseases. After a patient has undergone a total proctocolectomy, a procedure called ileal pouch-anal anastomosis (IPAA) is performed. In an IPAA, the ileum, or lowest part of the small intestine, is connected to the anus to create a structure (pouch) that can store and eliminate stools. IPAA creates a reservoir for the stools into the perineum where the rectum was, and restores functionality of the anus with stools passed under voluntary control of the patient. Pouchitis is an inflammation (swelling) of the pouch that occurs when the pouch becomes irritated and inflamed. The inflammation can cause increased bowel frequency, abdominal cramping or bloating, lower abdominal pain, or sometimes blood in the stool. The cause of pouchitis is not entirely clear, but it almost always occurs in patients with ulcerative colitis or another form of colitis, and sometimes in those with familial adenomatous polyposis (FAP), a genetic (inherited) condition in which many polyps form in the colon. Pouchitis is usually treated with a 14-day course of antibiotics. Acute pouchitis (an isolated episode of pouchitis) is generally treated with antibiotics, such as metronidazole, rifaximin or ciprofloxacin, often associated to anti-inflammatory drugs.

Spontaneous bacterial peritonitis (SBP) is defined as an ascitic fluid infection without an evident intra-abdominal surgically treatable source. The presence of SBP, which almost always occurs in patients with cirrhosis and ascites, is suspected because of suggestive signs and symptoms, such as fever, abdominal pain, or altered mental status, though some patients are asymptomatic and are detected when they undergo paracentesis after being admitted to the hospital for another reason. Patients who suffer from SBP display terrible prognosis and have one year mortality rate ranging from 50% to 90%. SBP is treated, and may be prevented, with antibiotics, such as betalactamic antibiotics or chinolones.

It is now well established that gut flora and chronic liver diseases are closely interrelated. This association is most evident at late stages of the disease: cirrhosis and impaired liver function are associated with intestinal bacterial overgrowth, small bowel dysmotility, increased gut permeability, and decreased immunological defenses, all of which promote bacterial translocation from the gut to the systemic circulation, leading to infections that in turn aggravate liver dysfunction in a vicious circle. Gut dysbiosis (i.e. alterations of the normal saprophytic gut microflora) has been implicated in chronic metabolic disorders such as obesity, metabolic syndrome, diabetes, and cardiovascular diseases. Non-alcoholic fatty liver disease (NAFLD) is the liver manifestation of the metabolic syndrome and thus evolves in the same context as these metabolic diseases. It is therefore not surprising that recent literature emphasizes a potential role for gut dysbiosis in the pathophysiology of NAFLD. Non-alcoholic fatty liver disease (NAFLD) is a common cause of chronic liver disease that is representative of the increasing prevalence of metabolic syndrome. Most patients with NAFLD exhibit non-progressive simple fatty liver, namely non-alcoholic fatty liver (NAFL). Non-alcoholic steatohepatitis (NASH) is a more severe form of NAFLD that is broadly defined by the presence of steatosis with inflammation and progressive fibrosis that ultimately leads to cirrhosis and hepatocellular carcinoma (HCC). A subset of patients with NAFLD develops NASH through poorly understood mechanisms. Increasing evidence has suggested the presence of correlations between intestinal microbiota, bacterial translocation and NAFLD incidence. Alterations in intestinal microbiota resulting from a high-fat diet can induce NASH and exacerbation of related HCC. Because current therapies for, hepatic encephalopathy, hepatic cirrhosis, pouchitis, spontaneous bacteriral peritonitis, NAFLD, NAFL and NASH have several drawbacks (low or limited effectiveness, insurgence of complications or adverse reactions, recurrence), there is a need for new treatments to be developed. In particular, because bacterial infections play a important role in the pathogenesis of these diseases, there is a significant needs for new antibiotic treatments effective in eradicating the infections and limiting the systemic exposure to the antibiotic drug.

U.S. Pat. No. 8,263,120B2 describes oral pharmaceutical compositions with controlled and/or programmed release containing at least one rifamycin SV, or a pharmaceutically acceptable salt thereof, having antimicrobial and/or antiinfectious activity such as rifamycin SV and/or metronidazole for the treatment of infections of the large intestine, in particular the colon, wherein their specific sterilizing action is required. In particular, the oral pharmaceutical compositions of U.S. Pat. No. 8,263,120B2 leave the bacterial flora present in the portions of small intestine unaltered, releasing the rifamycin SV, or a pharmaceutically acceptable salt thereof, solely in the colon, thus giving localized and restricted anti-infectious efficacy.

Rifamycin SV is currently under development for the treatment of the traveler's diarrhea (TD) and infectious colitis: it has been formulated in a gastro-protected tablet to avoid the exposure of the rifamycin SV, or a pharmaceutically acceptable salt thereof, to the gastric environment, where the acid pH could damage the integrity of the medicament thus decreasing the antibiotic effect of the administered dosage. Considering that the TD and the infectious colitis is mainly localized in the last part of the gastrointestinal tract, specifically in the colon, an early release of the rifamycin SV, or a pharmaceutically acceptable salt thereof, is not desired to avoid any possible exposition to the metabolic action of the enzymes present in the small intestine or in the stomach, and also the dilution of the drug in the aqueous fluids of the small intestine should be possibly avoided.

SUMMARY

The present invention relates to oral pharmaceutical compositions comprising rifamycin SV, or a pharmaceutically acceptable salt thereof, formulated to obtain an extended release profile of the rifamycin SV, or a pharmaceutically acceptable salt thereof. The extended release profile of the compositions of the present invention exhibits a release of the rifamycin SV, or a pharmaceutically acceptable salt thereof, starting in the proximal portion of the intestine, i.e. in the small intestine (duodenum, jejunum and ileum) and may optionally continue throughout the large intestine.

Oral pharmaceutical compositions of the invention are useful in the prevention and/or treatment of a disease or disorder such as cholera or small intestine bacterial overgrowth (SIBO) and/or irritable bowel syndrome (IBS).

Oral pharmaceutical compositions of the invention are also useful in the prevention and/or treatment of a disease or disorder such as hepatic encephalopathy, hepatic cirrhosis, pouchitis, spontaneous bacterial peritonitis, NAFLD, NAFL and/or NASH.

In one aspect are provided oral pharmaceuticals composition in the form of a solid dosage form comprising about 600 mg of rifamycin SV, or a pharmaceutically acceptable salt thereof, and one or more pharmaceutically acceptable excipients, wherein the oral pharmaceutical composition is formulated for modified release.

In one aspect are provided any of the oral pharmaceutical compositions disclosed herein, wherein the oral pharmaceutical composition is formulated for extended release.

In one aspect are provided any of the oral pharmaceutical compositions disclosed herein, wherein the oral pharmaceutical composition is formulated for delayed release.

In one aspect are provided any of the oral pharmaceutical compositions disclosed herein, wherein the oral pharmaceutical composition is formulated for delayed and extended release In one aspect are provided any of the oral pharmaceutical compositions disclosed herein, wherein the oral pharmaceutical composition is formulated to release the rifamycin SV, or a pharmaceutically acceptable salt thereof, substantially in the small intestine.

In one aspect are provided any of the oral pharmaceutical compositions disclosed herein for use in the prevention and/or treatment of small intestine bacterial overgrowth (SIBO).

In one aspect are provided any of the oral pharmaceutical compositions disclosed herein for use in the prevention and/or treatment of irritable bowel syndrome (IBS).

In one aspect are provided any of the oral pharmaceutical compositions disclosed herein for use in the prevention and/or treatment of irritable bowel syndrome with predominant diarrhea (IBS-D).

In one aspect are provided any of the oral pharmaceutical compositions disclosed herein for use in the prevention and/or treatment of intestinal bowel syndrome with alternated predominant diarrhea and constipation (IBS-M).

In one aspect are provided any of the oral pharmaceutical compositions disclosed herein for use in the prevention and/or treatment of cholera.

In one aspect are provided any of the oral pharmaceutical compositions disclosed herein for use in the prevention and/or treatment of hepatic encephalopathy.

In one aspect are provided any of the oral pharmaceutical compositions disclosed herein for use in the prevention and/or treatment of hepatic cirrhosis.

In one aspect are provided any of the oral pharmaceutical compositions disclosed herein for use in the prevention and/or treatment of pouchitis.

In one aspect are provided any of the oral pharmaceutical compositions disclosed herein for use in the prevention and/or treatment of spontaneous bacterial peritonitis.

In one aspect are provided any of the oral pharmaceutical compositions disclosed herein for use in the prevention and/or treatment of NAFLD.

In one aspect are provided any of the oral pharmaceutical compositions disclosed herein for use in the prevention and/or treatment of NAFL.

In one aspect are provided any of the oral pharmaceutical compositions disclosed herein for use in the prevention and/or treatment of NASH.

In one aspect is provided a method of treating and/or preventing small intestine bacterial overgrowth (SIBO) in a subject in need thereof, comprising administering to the subject an effective amount of any of the oral pharmaceutical composition disclosed herein.

In one aspect is provided a method of treating and/or preventing irritable bowel syndrome (IBS) in a subject in need thereof, comprising administering to the subject an effective amount of any of the oral pharmaceutical composition disclosed herein.

In one aspect is provided a method of treating and/or preventing irritable bowel syndrome (IBS) in a subject in need thereof, wherein the IBS has predominant diarrhea (IBS-D).

In one aspect is provided a method of treating and/or preventing irritable bowel syndrome (IBS) in a subject in need thereof, where the IBS has alternated predominant diarrhea or constipation (IBS-M).

In one aspect is provided a method of treating and/or preventing cholera in a subject in need thereof, comprising administering to the subject an effective amount of any of the oral pharmaceutical composition disclosed herein.

In one aspect is provided a method of treating and/or preventing hepatic encephalopathy in a subject in need thereof, comprising administering to the subject an effective amount of any of the oral pharmaceutical composition disclosed herein.

In one aspect is provided a method of treating and/or preventing hepatic cirrhosis in a subject in need thereof, comprising administering to the subject an effective amount of any of the oral pharmaceutical composition disclosed herein.

In one aspect is provided a method of treating and/or preventing pouchitis in a subject in need thereof, comprising administering to the subject an effective amount of any of the oral pharmaceutical composition disclosed herein.

In one aspect are is provided a method of treating and/or preventing spontaneous bacterial peritonitis in a subject in need thereof, comprising administering to the subject an effective amount of any of the oral pharmaceutical composition disclosed herein.

In one aspect is provided a method of treating and/or preventing NAFLD in a subject in need thereof, comprising administering to the subject an effective amount of any of the oral pharmaceutical composition disclosed herein.

In one aspect is provided a method of treating and/or preventing NAFL in a subject in need thereof, comprising administering to the subject an effective amount of any of the oral pharmaceutical composition disclosed herein.

In one aspect is provided a method of treating and/or preventing NASH in a subject in need thereof, comprising administering to the subject an effective amount of any of the oral pharmaceutical composition disclosed herein.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "amphiphilic," as used herein refers to an affinity for lipids and an affinity for water.

The terms "approximately" and "about" as used herein refers to the range of the experimental error, which may occur in a measurement, such as for example, 10%, 5%, 2.5%, 2% or 1% error.

The term "bioequivalent," has the meaning defined in 21 C.F.R. Section 314.3 and refers to the absence of a significant difference in the rate and extent to which the rifamycin becomes available at the site of drug action when administered at the same molar dose and under similar conditions. Two products may be considered bioequivalent if the 90% confidence interval of the relevant pharmacokinetic values of rifamycin observed in a subject when a given composition is administered to a subject is within about 80% to about 125% of the values observed for the reference product.

The term "cholera" used herein refers to a pathological condition known to those of ordinary skill in the art as being caused by the infection by the microorganism *Vibrio cholerae*.

The terms "comprising," "having," "including" and "containing" as used herein can be used interchangeably and are to be construed as open-ended terms (i.e. meaning "including, but not limited to") and are to be considered as providing support also for terms as "consist essentially of," "consisting essentially of," "consist of" or "consisting of".

The terms "consist essentially of," "consisting essentially of" as used herein can be used interchangeably and are to be construed as semi-closed terms, meaning that no other ingredients which materially affects the basic and novel characteristics of the invention are included (optional excipients may thus be included).

The terms "consists of," "consisting of" as used herein can be used interchangeably and are to be construed as a closed term.

The term "core" refers to a matrix, mixture, compressed blend or dispersion of the rifamycin SV, or a pharmaceutically acceptable salt thereof, at least one lipophilic compound, at least one hydrophilic compound and optionally at least one amphiphilic compound and optionally at least one physiologically acceptable excipient.

The term "delayed release," as used herein in relation to a dosage form, describes a dosage form that releases a drug (or drugs) at a time other than immediately following oral administration of the dosage form to a subject.

The term "extended release," as used herein in relation to a dosage form, describes a dosage form formulated to make a drug available over an extended period of time after oral administration of the dosage form to a subject.

The term "gastro-resistant coating," as used herein, refers to a coating that allows a composition, such as a solid oral dosage form such as a tablet, to pass through the gastric tract, such as the stomach, without being damaged or eroded and which then beings dissolving or eroding, or dissolves or erodes substantially or completely, with the consequent release of the rifamycin SV, or a pharmaceutically acceptable salt thereof, comprising the dosage form, such as when the environmental conditions change as, for example, when the pH of the gastrointestinal tract changes. The coating may be applied directly to the core.

The term "hydrophilic," as used herein, refers to an affinity for water.

The terms "IBS" and "irritable bowel syndrome" as used herein after refer to conditions known to those of ordinary skill in the art as functional bowel disorders that can result in abdominal pain, bloating, and altered bowel function (diarrhea, constipation, or both). The term "IBS" used herein includes IBS-C (constipation predominant), IBS-D (diarrhea predominant), IBS-M (mixed type) and IBS-U (uncategorized).

The terms "large intestine" as used herein refer to the last part of the gastrointestinal tract or the digestive system. The large intestine includes the cecum, colon, rectum, and anal canal.

The term "lipophilic," as used herein, refers to an affinity for lipids and a poor affinity for aqueous fluids.

The term "matrix" as used herein refers to a macroscopically homogeneous structure when ideally cut in all its axes or in all its volume. The term "homogenous" does not require that the excipients in the core are homogenously dispersed or homogeneously mixed, but is meant to describe the absence of discrete layers in the core structure.

The term "mixture" as used herein refers to a composition formed by or produced by mixing two or more substances wherein the substances are mixed together but not chemically united into a new substance.

The term "modified release," as used herein in relation to a dosage, describes a dosage form whose drug-release characteristics of time course and/or location are chosen to accomplish therapeutic or convenience objectives not offered by conventional dosage forms such as a solution or an immediate release dosage form. Modified release solid oral dosage forms include both delayed and extended release drug products.

The term "pharmaceutically acceptable salts" as used herein refers to those salts which possess the biological effectiveness and properties of the salified compound and which do not produce adverse reactions when administered to a mammal, preferably a human. The pharmaceutically acceptable salts may be inorganic or organic salts; examples of pharmaceutically acceptable salts include but are not limited to: sodium, potassium, magnesium, carbonate, hydrogen carbonate chloride, bromide, sulphate, hydrogen sulphate, citrate, maleate, fumarate, trifluoroacetate, 2-naphthalenesulphonate, and para-toluenesulphonate. In one embodiment, the pharmaceutically acceptable salt is sodium. Further information on pharmaceutically acceptable salts can be found in *Handbook of pharmaceutical salts*, P. Stahl, C. Wermuth, WILEY-VCH, 127-133, 2008, herein incorporated by reference.

The term "physiologically acceptable excipient" as used herein refers to a substance devoid of any pharmacological effect of its own and which does not produce adverse reactions when administered to a mammal, preferably a human. Physiologically acceptable excipients are well known in the art and are disclosed, for instance in the *Handbook of Pharmaceutical Excipients*, sixth edition 2009, herein incorporated by reference.

The term "rifamycin B," as used herein, refers to the chemical compound having the Chemical Abstracts No. 13929-35-6 and the chemical name 4-O-(carboxymethyl) rifamycin; [(1,2-dihydro-5,6,17,19,21-pentahydroxy-23-methoxy-2,4,12,16,18,20,22-heptamethyl-1,11-dioxo-2,7-(epoxypentadeca[1,11,13]trienimino)naphtho[2,1-b]furan-9-yl)oxy]acetic acid 21-acetate.

The term "rifamycin S," as used herein, refers to the chemical compound having the Chemical Abstracts No. 13553-79-2 and the chemical name 5,17,19,21-Tetrahydroxy-23-methoxy-2,4,12,16,18,20,22-heptamethyl-2,7-(epoxypentadeca[1,11,13]trienimino)naphtho [2,1-b]furan-1,6,9,11(2H)-tetrone 21-acetate.

The terms "rifamycin SV," and "rifamycin" as used herein are interchangeable, and refer to the chemical compound having the Chemical Abstracts No. 6998-60-3 and the chemical name (2S,12Z,14E,16S,17S,18R,19R,20R,21S,22R,23S,24E)-21-(acetyloxy)-6,9,17,19-tetrahydroxy-23-methoxy-2,4,12,16,18,20,22-heptamethyl-1,11-dioxo-1,2-dihydro-2,7-(epoxypentadeca [1,11,13]trienimino)naphtho [2,1-b]furan-5-ol, and (2S,12Z,14E,16S,17S ,18R,19R,20R, 21S,22R,23S,24E)-5,6,9,17,19-pentahydroxy-23-methoxy-2,4,12,16,18,20,22-heptamethyl-1,11-dioxo-1,2-dihydro-2, 7-(epoxypentadeca [1,11,13]trienoimino)naphtho[2,1-b] furan-21-yl acetate.

The terms "rifamycin sodium," "rifamycin sodium salt," "sodium rifamycin," "rifamycin SV sodium," "rifamycin SV sodium salt", and "sodium rifamycin SV" as used herein are interchangeable, and refer to the sodium salt of rifamycin SV, having the Chemical Abstracts No. 14897-39-3.

The expression "600 mg of rifamycin SV or a pharmaceutically acceptable salt thereof" herein refers to an amount of 600 mg of rifamycin SV as dry substance (anhydrous) or to 600 mg of a pharmaceutically salt of rifamycin SV as dry substance, including, but not limited to, an amount of 600 mg of the sodium salt of rifamycin SV, or to an amount of a pharmaceutically acceptable salt of rifamycin SV which is equivalent to 600 mg of rifamycin SV as dry substance (anhydrous). In one aspect, 600 mg of the sodium salt of rifamycin SV as dry substance are equivalent to 582 mg of rifamycin SV as dry substance. In one aspect, 600 mg of the sodium salt of rifamycin SV are equivalent to 582 mg of rifamycin SV and 18 mg of sodium ions.

As used herein, the terms "prevent," "prevention," and "preventing" refer to the reduction or inhibition in the risk of acquiring or developing a given condition, or the reduction or inhibition of the recurrence or said condition in a subject who is not ill, but who has been or may be near a person with a disease or disorder.

The terms "SIBO" and "small intestinal bacterial overgrowth" as used herein after refer to conditions known to those of ordinary skill in the art as small intestinal bacterial overgrowth, is a disturbance of the normal GI flora. In SIBO the concentration of bacterial organisms in the terminal jejunum and ileum is increased, and the normal distribution of bacteria is perturbed. In SIBO there is an increased number and/or type of bacteria in the small bowel. A finding of $\leq 10^5$ CFU of bacteria per ml of proximal jejunal aspirate is typical, wherein under normal conditions, the bacterial concentration in the small intestine is not higher than $10^2$.

The term "small intestine" as used herein refers to the proximal part of the intestine that is the area of the gastrointestinal tract between the stomach and the large intestine, and is where most of the end absorption of food takes place. The small intestine has three distinct regions—the duodenum, jejunum, and ileum.

The terms "treat," "treatment," and "treating" as used herein, refer to therapeutic treatments. For example, therapeutic treatments include the reduction or amelioration of the progression, severity and/or duration of a disease or disorder mediated conditions, or the amelioration of one or more symptoms (specifically, one or more discernible symptoms) of a disease or disorder mediated conditions, resulting from the administration of one or more therapies (e.g., one or more therapeutic agents such as a composition of the invention). In specific embodiments, the therapeutic treatment includes the amelioration of at least one measurable physical parameter of a disease or disorder mediated condition. In other embodiments the therapeutic treatment includes the inhibition of the progression of a disease or disorder mediated condition, either physically by, e.g., stabilization of a discernible symptom, physiologically by, e.g., stabilization of a physical parameter, or both. In other embodiments the therapeutic treatment includes the reduction or stabilization of a disease or disorder mediated symptoms.

"$C_{max,0-6}$": Maximum plasma concentration achieved in the selected interval (0-6 hours).

"$C_{max,0-24}$": Maximum plasma concentration achieved in the selected interval (0-24 hours).

"$t_{max,0-6}$": Time to achieve $C_{max,0-6}$.

"$t_{max,0-24}$": Time to achieve $C_{max,0-24}$.

"$\lambda z$": Terminal elimination rate constant, calculated after first dose, if feasible, by log-linear regression using at least three points.

"$t_{1/2}$": Half-life, calculated after first dose, if feasible, as $\ln 2/\lambda_z$.

"$AUC_{0-6}$": Area under the concentration/time curve during the selected interval (0-6 hours) calculated with trapezoidal method.

"$AUC_{0-24}$": Area under the concentration/time curve during the selected interval (0-24 hours) calculated with trapezoidal method.

"$AUC_{0-\infty}$": Area under the concentration-time curve extrapolated to infinity, calculated after first dose, if feasible, as $AUC_{0-6}+C_t\lambda_z$, where Ct is the last measurable drug concentration.

"$Cl_t/F$": Total body clearance, calculated after first dose, if feasible, as $Dose/AUC_{0-\infty}$.

"$Cl_r$": Renal clearance, calculated after first dose as Ae0-6/AUC0-6.

"$V_z/F$": Apparent terminal volume of distribution, calculated after first dose, if feasible, as $Dose/\lambda_z x\, AUC_{0-\infty}$.

"$C_{max,ss,12-18}$": Maximum plasma concentration in the selected interval (12-18 hours) achieved at steady state.

"$C_{min,ss,12-18}$": Minimum plasma concentration in the selected interval (12-18 h) achieved at steady state.

"$AUC_{ss,12-18}$": Area under the concentration/time curve during the selected interval (12-18 hours) at steady state calculated with trapezoidal method.

"$AUC_{ss,0-24}$": Area under the concentration/time curve during the selected interval (0-24 hours) at steady state calculated with trapezoidal method.

"$t_{max,ss,12-18}$": Time to achieve $C_{max,ss,12-18}$. "$C_{ave,12-18}$": Average plasma concentration in the selected interval (12-18 hours), calculated as $AUC_{ss,12-18}/\tau$, where $\tau$ is the dosing interval (6 hours).

"PTF $\%_{12-18}$": Peak-trough fluctuation, calculated in the selected interval (12-18 hours) as $$\frac{C_{max,ss12-18} - C_{min,ss12-18}}{C_{ave,12-18}} \times 100$$

"$Ae_{0-24}$": Total amount of analyte excreted in urine during the selected interval (24 h).

"% $Ae_{0-24}$": Percentage amount of analyte excreted in urine, calculated as ($Ae_{0-24}$/dose×3)×100.

$EC_{50}$: Half maximal effective concentration: it refers to the concentration of the tested compound, which induces a response halfway between the baseline and maximum response.

$IC_{50}$: Half maximal inhibitory concentration: it refers to the concentration of the tested compound, which inhibits a response halfway between the baseline and maximum response.

DETAILED DESCRIPTION

Figure 1:
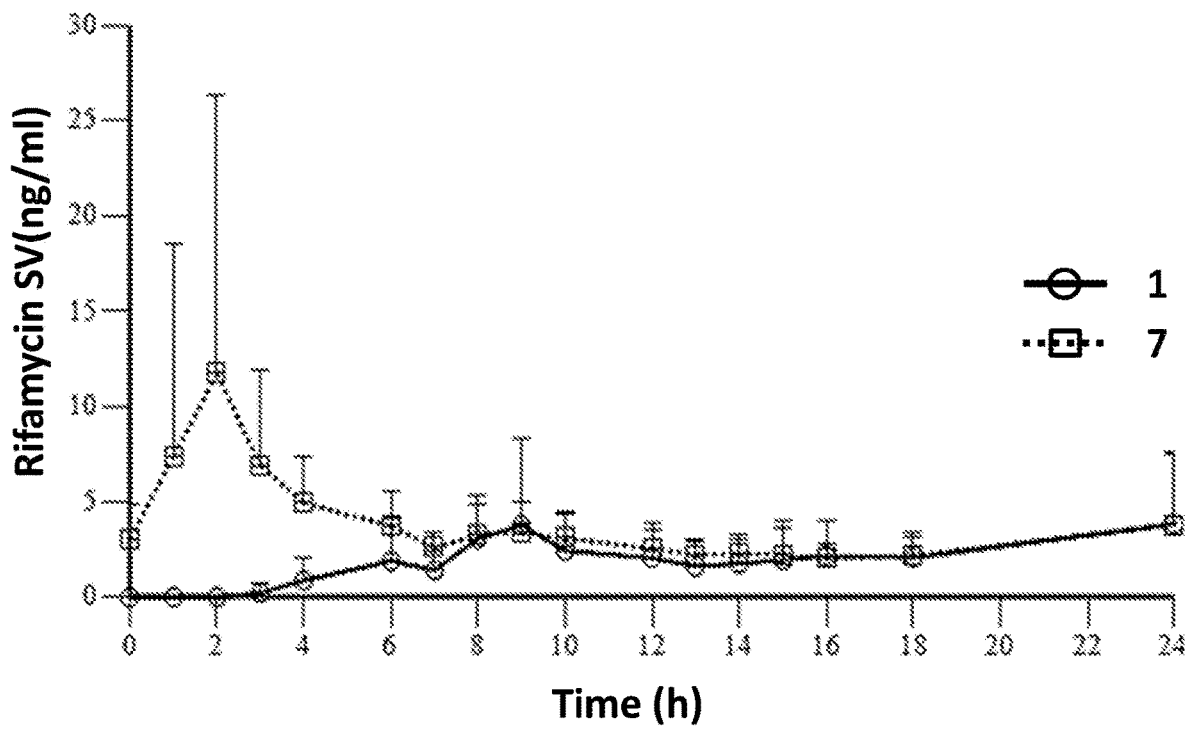
FIG. 1: Shows the mean (±the standard deviation (SD)) rifamycin SV concentration (ng/mL) vs. time profiles at Day 1 and Day 7 during a study treatment of healthy volunteers with the test rifamycin SV 600 mg coated tablet according to the invention reported in the experimental section. 1: rifamycin SV concentrations vs. time on day 1 (●); 7: rifamycin SV concentrations vs. time on day 7 (□).
Figure 2:
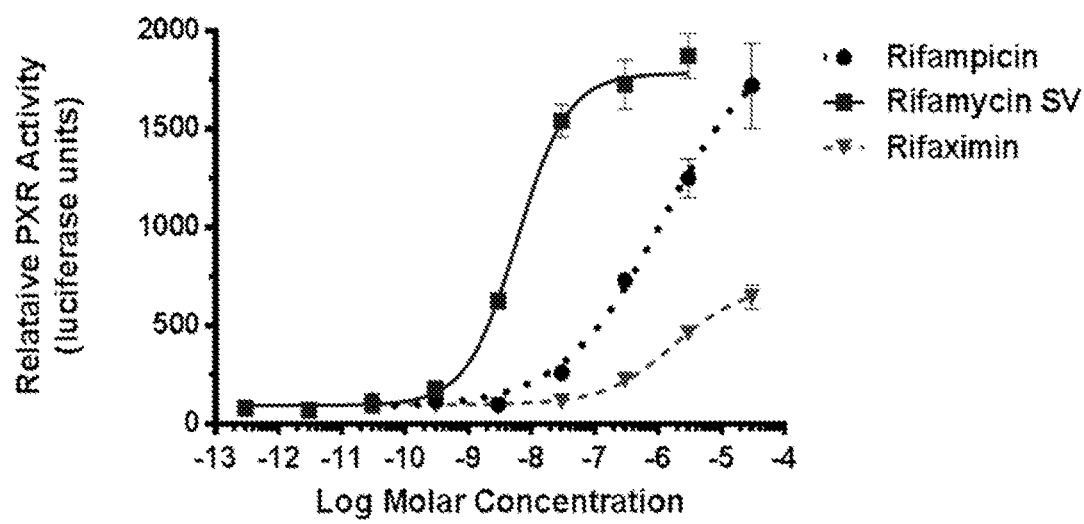
FIG. 2: Shows rifamycin SV stimulation of PXR transcriptional activity. Rifamycin SV (■) activity is compared to rifaximin (▼) and rifampicin (●) (used as control) in this test. Data were calculated from 3 independent experiments.
Figure 3:
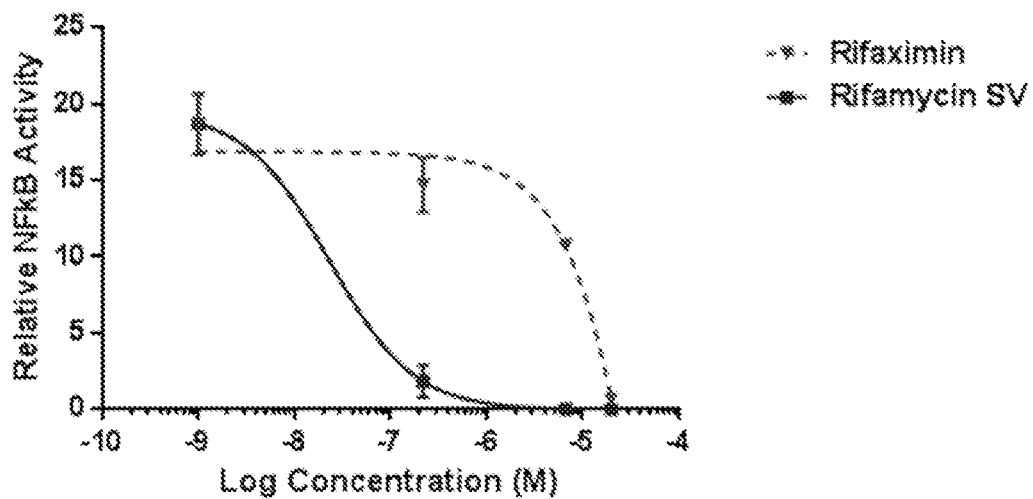
FIG. 3: Shows rifamycin SV inhibition NFkB activity (induced by TNFα). In the test rifamycin SV (■) activity is compared to rifaximin (▼), a drug that obtained approval from FDA for IBS-D. Data were calculated from 2 independent experiments.

In one aspect is provided an oral pharmaceutical composition in the form of a solid dosage form comprising about 600 mg of rifamycin SV, or a pharmaceutically acceptable salt thereof, and one or more pharmaceutically acceptable excipients, wherein the oral pharmaceutical composition is formulated for modified release. In one aspect, 600 mg of the sodium salt of rifamycin SV as a dry substance is equivalent to 582 mg of rifamycin SV as a dry substance.

In one aspect are provided any of the oral pharmaceutical compositions disclosed herein, wherein the oral pharmaceutical composition is formulated for extended release.

In one aspect are provided any of the oral pharmaceutical compositions disclosed herein, wherein the oral pharmaceutical composition is formulated for delayed release.

In one aspect are provided any of the oral pharmaceutical compositions disclosed herein, wherein the oral pharmaceutical composition is formulated for delayed and extended release.

In one aspect are provided any of the oral pharmaceutical compositions disclosed herein, wherein the oral pharmaceutical composition is formulated to release the rifamycin SV, or a pharmaceutically acceptable salt thereof, substantially in the small intestine.

In one aspect are provided any of the oral pharmaceutical compositions disclosed herein, wherein the oral pharmaceutical composition is formulated to release the rifamycin SV, or a pharmaceutically acceptable salt thereof, substantially following passage of the solid dosage form into the pylorus passage in the proximal part of the intestine.

In one aspect are provided any of the oral pharmaceutical compositions disclosed herein, further comprising one or more of a lipophilic compound, a hydrophilic compound and an amphiphilic compound.

In one aspect are provided any of the oral pharmaceutical compositions disclosed herein, further comprising one or more lipophilic compound.

In one aspect are provided any of the oral pharmaceutical compositions disclosed herein, further comprising one or more hydrophilic compound.

In one aspect are provided any of the oral pharmaceutical compositions disclosed herein, further comprising one or more amphiphilic compound.

In one aspect are provided any of the oral pharmaceutical compositions disclosed herein, further comprising one or more lipophilic compound and one or more hydrophilic compound.

In one aspect are provided any of the oral pharmaceutical compositions disclosed herein, further comprising one or more lipophilic compound and one or more amphiphilic compound.

In one aspect are provided any of the oral pharmaceutical compositions disclosed herein, further comprising one or more hydrophilic compound and one or more amphiphilic compound.

In one aspect are provided any of the oral pharmaceutical compositions disclosed herein, further comprising a gastro-resistant coating.

In one aspect are provided any of the oral pharmaceutical compositions disclosed herein, wherein the rifamycin SV, or a pharmaceutically acceptable salt thereof, is released from the solid dosage form when the solid dosage form is placed in an aqueous medium having a pH in the range of about pH 5 to about pH 7.5. In other aspects are provided any of the oral pharmaceutical compositions disclosed herein, wherein the rifamycin SV, or a pharmaceutically acceptable salt thereof, is released from the solid dosage form when the solid dosage form is placed in an aqueous medium having a pH in the range of about pH 5 to about pH 7, or from about pH 5 to about pH 6.5, or from about pH 5 to about pH 6.

In one aspect are provided any of the oral pharmaceutical compositions disclosed herein, wherein the solid dosage form comprises a core and a gastro-resistant coating covering the core. In one aspect, the core is a matrix, mixture, compressed blend or a dispersion of the ingredients found in the core. In one aspect the coating is applied directly on the core. In one embodiment, the core may also comprise one or more of microcrystalline cellulose, lactose (such as lactose monohydrate), colloidal silicon dioxide, povidone and/or co-povidone, and microcrystalline cellulose.

In one aspect are provided any of the oral pharmaceutical compositions disclosed herein, wherein the administration of one or more of the solid dosage forms to a subject exhibits in a $t_{max,0-24}$ of the rifamycin SV in the plasma of the subject of about 9.50 hours.

In one aspect are provided any of the oral pharmaceutical compositions disclosed herein, wherein the administration of three or more of the solid dosage forms to a subject exhibits a $C_{max,0-6}$ of the rifamycin SV in the plasma of the subject of about 2.19±1.94 ng/mL. In one aspect are provided any of the oral pharmaceutical compositions disclosed herein, wherein the administration of three or more of the solid dosage forms to a subject exhibits a $C_{max,0-6}$ of the rifamycin SV in the plasma of the subject greater than about 2.19 ng/mL.

In one aspect are provided any of the oral pharmaceutical compositions disclosed herein, wherein the administration of three or more of the solid dosage forms to a subject exhibits a $C_{max,0-24}$ of the rifamycin SV in the plasma of the subject of about 5.79±4.24 ng/mL. In one aspect are provided any of the oral pharmaceutical compositions disclosed herein, wherein the administration of three or more of the solid dosage forms to a subject exhibits a $C_{max,0-24}$ of the rifamycin SV in the plasma of the subject greater than about 5.79 ng/mL.

In one aspect are provided any of the oral pharmaceutical compositions disclosed herein, wherein the administration of three or more of the solid dosage forms to a subject exhibits an $AUC_{0-6}$ of the rifamycin SV in the plasma of the subject of about 3.26±2.85 (ng)(h)/mL. In one aspect are provided any of the oral pharmaceutical compositions disclosed herein, wherein the administration of three or more of the solid dosage forms to a subject exhibits an $AUC_{0-6}$ of the rifamycin SV in the plasma of the subject greater than about 3.26 (ng)(h)/mL.

In one aspect are provided any of the oral pharmaceutical compositions disclosed herein, wherein the administration of three or more of the solid dosage forms to a subject exhibits an $AUC_{0-24}$ of the rifamycin SV in the plasma of the subject of about 43.67±20.15 (ng)(h)/mL. In one aspect are provided any of the oral pharmaceutical compositions disclosed herein, wherein the administration of three or more of the solid dosage forms to a subject exhibits an $AUC_{0-24}$ of the rifamycin SV in the plasma of the subject greater than about 43.67 (ng)(h)/mL.

In one aspect are provided any of the oral pharmaceutical compositions disclosed herein, wherein the administration of the oral pharmaceutical composition to a subject exhibits an AUC and/or $C_{max}$ of the rifamycin SV in the plasma of the subject that is within about 80% to 125% of the values disclosed herein.

In one aspect are provided an oral pharmaceutical composition that is bioequivalent to any of the oral pharmaceutical compositions disclosed herein.

In one aspect are provided any of the oral pharmaceutical compositions disclosed herein, wherein it provides a urine elimination rate of the rifamycin SV in a subject to which the oral pharmaceutical composition is administered of not more than about 1% of the total amount of rifamycin SV, or a pharmaceutically acceptable salt thereof, administered to the subject.

In one aspect are provided any of the oral pharmaceutical compositions disclosed herein, wherein said pharmaceutical composition releases not more than about 10% of the amount of rifamycin SV, or a pharmaceutically acceptable salt thereof, comprising the pharmaceutical composition when the pharmaceutical composition is placed in a USP dissolution apparatus II complying with USP <711> for 2 hours, wherein the dissolution apparatus comprises 1000 mL of an aqueous solution comprising 0.1 M hydrochloric acid and 0.4% macrogol cetostearyl ether at pH 1 and at a temperature of 37±0.5° C., and wherein the aqueous solution is stirred at a rate of 50 rpm. In other aspects are provided any of the oral pharmaceutical compositions disclosed herein, wherein the pharmaceutical composition releases not more than about 5%, not more than about 2.5%, not more than about 2%, or not more than about 1% of the amount of rifamycin SV, or a pharmaceutically acceptable salt thereof, comprising the pharmaceutical composition when the pharmaceutical composition is placed in the USP dissolution apparatus II complying with USP <711> for 2 hours, wherein the dissolution apparatus comprises 1000 mL of an aqueous solution comprising 0.1 M hydrochloric acid and 0.4% macrogol cetostearyl ether at pH 1 and at a temperature of 37±0.5° C., and wherein the aqueous solution is stirred at a rate of 50 rpm.

In one aspect are provided any of the oral pharmaceutical compositions disclosed herein, wherein the pharmaceutical composition releases not more than about 20% of the amount of rifamycin SV, or a pharmaceutically acceptable salt thereof, comprising the pharmaceutical composition when the pharmaceutical composition is placed in a USP dissolution apparatus II complying with USP <711> for 1 hour, wherein the dissolution apparatus comprises 900 mL of an aqueous buffer at pH 6.4 and at a temperature of 37±0.5° C., and wherein the aqueous solution is stirred at a rate of 100 rpm. In one aspects are provided any of the oral pharmaceutical compositions disclosed herein, wherein the pharmaceutical composition releases not more than about 15%, not more than about 10%, not more than about 5%, not more than about 2.5%, not more than about 2%, or not more than about 1% of the amount of rifamycin SV, or a pharmaceutically acceptable salt thereof, comprising the pharmaceutical composition when the pharmaceutical composition is placed in a USP dissolution apparatus II complying with USP <711> for 1 hour, wherein the dissolution apparatus comprises 900 mL of an aqueous buffer at pH 6.4 and at a temperature of 37±0.5° C., and wherein the aqueous solution is stirred at a rate of 100 rpm.

In one aspect are provided any of the oral pharmaceutical compositions disclosed herein, wherein the pharmaceutical composition releases between about 20% and about 60% of the amount of rifamycin SV, or a pharmaceutically acceptable salt thereof, comprising the pharmaceutical composition when the pharmaceutical composition is placed in a USP dissolution apparatus II complying with USP <711> for 3 hours, wherein the dissolution apparatus comprises 900 mL of an aqueous buffer at pH 6.4 and at a temperature of 37±0.5° C., and wherein the aqueous solution is stirred at a rate of 100 rpm.

In one aspect are provided any of the oral pharmaceutical compositions disclosed herein, wherein the pharmaceutical composition releases not less than about 50% of the amount of rifamycin SV, or a pharmaceutically acceptable salt thereof, comprising the pharmaceutical composition when the pharmaceutical composition is placed in a USP dissolution apparatus II complying with USP <711> for 6 hours, wherein the dissolution apparatus comprises 900 mL of an aqueous buffer at pH 6.4 and at a temperature of 37±0.5° C., and wherein the aqueous solution is stirred at a rate of 100 rpm. In other aspects are provided any of the oral pharmaceutical compositions disclosed herein, wherein the pharmaceutical composition releases not less than about 60%, not less than about 70%, not less than about 75%, not less than about 80%, not less than about 85%, not less than about 90%, or not less than about 95% of the amount of rifamycin SV, or a pharmaceutically acceptable salt thereof, comprising the pharmaceutical composition when the pharmaceutical composition is placed in the USP dissolution apparatus II complying with USP <711> for 6 hours, wherein the dissolution apparatus comprises 900 mL of an aqueous buffer at pH 6.4 and at a temperature of 37±0.5° C., and wherein the aqueous solution is stirred at a rate of 100 rpm.

In one aspect are provided any of the oral pharmaceutical compositions disclosed herein, wherein the pharmaceutical composition contains no more than about 2 wt % of rifamycin S. In other aspects are provided any of the oral pharmaceutical compositions disclosed herein, wherein the composition contains no more than about 1.5 wt %, no more than about 1.25 wt %, no more than about 1 wt %, no more than about 0.75 wt %, no more than about 0.5 wt %, no more than about 0.25 wt %, no more than about 0.2 wt %, no more than about 0.1 wt %, or no more than about 0.05 wt % of rifamycin S.

In one aspect are provided any of the oral pharmaceutical compositions disclosed herein, wherein the pharmaceutical composition contains no more than about 1 wt % of rifamycin B. In other aspects are provided any of the oral pharmaceutical compositions disclosed herein, wherein the pharmaceutical composition contains no more than about 0.75 wt %, no more than about 0.5 wt %, no more than about 0.25 wt %, no more than about 0.2 wt %, no more than about 0.15 wt %, or no more than about 0.1 wt % of rifamycin B.

In one aspect are provided any of the oral pharmaceutical compositions disclosed herein, wherein the pharmaceutical composition contains no more than 10,000 parts per million of ethanol. In other aspects are provided any of the oral pharmaceutical compositions disclosed herein, wherein the pharmaceutical composition contains no more than 7,500 parts per million, no more than 7,000 parts per million, no more than 6,000 parts per million, no more than 5,500 parts per million, no more than 5,000 parts per million, or no more than 4,500 parts per million of ethanol.

In one aspect are provided any of the oral pharmaceutical compositions disclosed herein, wherein the solid dosage form contains less than about 2 wt % of rifamycin S following storage of the solid dosage form at 25° C. and 60% relative humidity for 3 months. In other aspects are provided any of the oral pharmaceutical compositions disclosed herein, wherein the solid dosage form contains less than about 1 wt %, less than about 0.75 wt %, less than about 0.5 wt %, %, less than about 0.25 wt %, or less than about 0.1 wt % of rifamycin S following storage of the solid dosage form at 25° C. and 60% relative humidity for 3 months.

In one aspect are provided any of the oral pharmaceutical compositions disclosed herein, wherein the solid dosage form contains less than about 2 wt % of rifamycin S following storage of the solid dosage form at 40° C. and 75% relative humidity for 1 month. In other aspects are provided any of the oral pharmaceutical compositions disclosed herein, wherein the solid dosage forms contain less than less than about 1.75 wt %, less than about 1.5 wt %, less than about 1.25 wt %, less than about 1 wt %, less than about 0.75 wt %, less than about 0.5 wt %, less than about 0.25 wt %, or less than about 0.1 wt % of rifamycin S following storage of the solid dosage form at 40° C. and 75% relative humidity for 1 month.

In one aspect are provided any of the oral pharmaceutical compositions disclosed herein, wherein the solid dosage form contains less than 1 wt % of rifamycin B following storage of the solid dosage form at 40° C. and 75% relative humidity for 1 month. In other aspects are provided any of the oral pharmaceutical compositions disclosed herein, wherein the solid dosage forms contain less than less than about 0.75 wt %, less than about 0.5 wt %, less than about 0.25 wt %, or less than about 0.1 wt % of rifamycin B following storage of the solid dosage form at 40° C. and 75% relative humidity for 1 month.

In one aspect are provided any of the oral pharmaceutical compositions disclosed herein, wherein the solid dosage form contains less than 2 wt % of rifamycin S following storage of the solid dosage form at 30° C. and 65% relative humidity for 1 month. In other aspects are provided any of the oral pharmaceutical compositions disclosed herein, wherein the solid dosage forms contain less than less than about 1.75 wt %, less than about 1.5 wt %, less than about 1.25 wt %, less than about 1 wt %, less than about 0.75 wt %, less than about 0.5 wt %, less than about 0.25 wt %, or less than about 0.1 wt % of rifamycin S following storage of the solid dosage form at 30° C. and 65% relative humidity for 1 month. All the above wt % of rifamycin S are measured with respect to the amount of rifamycin SV (as labeled claim) present in the composition.

In one aspect are provided any of the oral pharmaceutical compositions disclosed herein, wherein the solid dosage form contains less than 1 wt % of rifamycin B following storage of the solid dosage form at 30° C. and 65% relative humidity for 1 month. In other aspects are provided any of the oral pharmaceutical compositions disclosed herein, wherein the solid dosage forms contain less than less than about 0.75 wt %, less than about 0.5 wt %, less than about 0.25 wt %, or less than about 0.1 wt % of rifamycin B following storage of the solid dosage form at 30° C. and 65% relative humidity for 1 month. In some embodiments, the solid dosage form contains less than 1 wt % of rifamycin B following storage of the solid dosage form at 25° C. and 60% relative humidity for 3 months.

In the embodiments described above, the wt % of rifamycin S and rifamycin B are expressed as the amount of the rifamycin S and rifamycin B, respectively, divided by the labeled claim amount of rifamycin SV in the composition. For example, a composition intended to comprise 600 mg of sodium rifamycin SV would have a labeled claim amount of sodium rifamycin SV of 600 mg. Such a labeled claim amount of sodium rifamycin SV of 600 mg may also or alternatively correspond to a labeled claim amount of 582 mg of rifamycin SV.

In one aspect are provided any of the oral pharmaceutical compositions disclosed herein, wherein the solid dosage form is contained in a package, wherein the package comprises materials to protect the solid dosage form from heat and light. In one aspect are provided any of the oral pharmaceutical compositions disclosed herein, wherein the package comprises aluminum. In one aspect are provided any of the oral pharmaceutical compositions disclosed herein, wherein the package comprises aluminum blister packages.

In one aspect are provided any of the oral pharmaceutical compositions disclosed herein, wherein the solid dosage form is in the form of a tablet. In one aspect are provided any of the oral pharmaceutical compositions disclosed herein, wherein the tablet comprises a tablet core and a gastro-resistant coating covering said tablet core. In one aspect are provided any of the oral pharmaceutical compositions disclosed herein, wherein the gastro-resistant coating comprises one or more of an acrylic acid polymer, an acrylic acid co-polymer, a methacrylic acid polymer, and a methacrylic acid copolymer. In one aspect are provided any of the oral pharmaceutical compositions disclosed herein, wherein the gastro-resistant coating is applied to the tablet core using a coating composition. In one aspect are provided any of the oral pharmaceutical compositions disclosed herein, wherein the coating composition comprises one or more of an organic solvent and water. In one aspect are provided any of the oral pharmaceutical compositions disclosed herein, wherein the organic solvent comprises one or more of one or more organic alcohol. In one aspect are provided any of the oral pharmaceutical compositions disclosed herein, wherein the one or more organic alcohol is selected from one or more of ethanol and polyethylene glycol. In one aspect are provided any of the oral pharmaceutical compositions disclosed herein, wherein the coating composition substantially excludes water. In one aspect are provided any of the oral pharmaceutical compositions disclosed herein, wherein the coating composition substantially excludes ethanol.

In one aspect are provided any of the oral pharmaceutical compositions disclosed herein for use in the prevention of the occurrence/recurrence of and/or treatment of small intestine bacterial overgrowth (SIBO).

In one aspect are provided any of the oral pharmaceutical compositions disclosed herein for use in the prevention of the occurrence/recurrence of and/or treatment of irritable bowel syndrome (IBS).

In one aspect are provided any of the oral pharmaceutical compositions disclosed herein for use in the prevention of the occurrence/recurrence of and/or treatment of irritable bowel syndrome with predominant diarrhea (IBS-D).

In one aspect are provided any of the oral pharmaceutical compositions disclosed herein for use in the prevention of the occurrence/recurrence of and/or treatment of intestinal bowel syndrome with alternated predominant diarrhea and constipation (IBS-M).

In one aspect are provided any of the oral pharmaceutical compositions disclosed herein for use in the prevention of the occurrence/recurrence of and/or treatment of cholera.

In one aspect are provided any of the oral pharmaceutical compositions disclosed herein for use in the prevention of the occurrence/recurrence of and/or treatment of hepatic encephalopathy. In one aspect are provided any of the oral pharmaceutical compositions disclosed herein for use in the reduction in risk of overt hepatic encephalopathy (HE) recurrence and/or reduction in the risk of breakthrough overt HE recurrence.

In one aspect are provided any of the oral pharmaceutical compositions disclosed herein for use in the prevention of the occurrence/recurrence of and/or treatment of hepatic cirrhosis.

In one aspect are provided any of the oral pharmaceutical compositions disclosed herein for use in the prevention of the occurrence/recurrence of and/or treatment of pouchitis.

In one aspect are provided any of the oral pharmaceutical compositions disclosed herein for use in the prevention of the occurrence/recurrence of and/or treatment of spontaneous bacterial peritonitis.

In one aspect are provided any of the oral pharmaceutical compositions disclosed herein for use in the prevention of the occurrence/recurrence of and/or treatment of NAFLD.

In one aspect are provided any of the oral pharmaceutical compositions disclosed herein for use in the prevention of the occurrence/recurrence of and/or treatment of NAFL.

In one aspect are provided any of the oral pharmaceutical compositions disclosed herein for use in the prevention of the occurrence/recurrence of and/or treatment of NASH.

In one aspect are provided any of the oral pharmaceutical compositions disclosed herein, wherein the oral pharmaceutical composition is administered to a subject at a daily dose of about 600 mg, about 1200 mg or about 1800 mg of a pharmaceutically acceptable salt of rifamycin SV. In one aspect are provided any of the oral pharmaceutical compositions disclosed herein, wherein the oral pharmaceutical composition comprises the sodium salt of rifamycin SV and is administered to a subject at a daily dose equivalent to about 582 mg, about 1164 mg or about 1746 mg of rifamycin SV.

In one aspect are provided any of the oral pharmaceutical compositions disclosed herein, wherein the composition is administered to a subject once, twice, or three times daily.

In one aspect is provided a method of treating and/or preventing small intestine bacterial overgrowth (SIBO) in a subject in need thereof, comprising administering to the subject an effective amount of any of the oral pharmaceutical compositions disclosed herein.

In one aspect is provided a method of treating and/or preventing irritable bowel syndrome (IBS) in a subject in need thereof, comprising administering to the subject an effective amount of comprising administering to the subject an effective amount of any of the oral pharmaceutical compositions disclosed herein. In one aspect is provided a method of treatment, wherein the IBS has predominant diarrhea (IBS-D). In one aspect is provided a method of treatment, wherein the IBS has alternated predominant diarrhea or constipation (IBS-M).

In one aspect is provided a method of treating cholera in a subject in need thereof, comprising administering to the subject an effective amount of any of the oral pharmaceutical compositions disclosed herein.

In one aspect is provided a method of treating and/or preventing hepatic encephalopathy in a subject in need thereof, comprising administering to the subject an effective amount of any of the oral pharmaceutical compositions disclosed herein. In one aspect is provided a method of reducing the risk of overt hepatic encephalopathy (HE) recurrence in a subject in need thereof, and/or reducing the risk of breakthrough overt HE recurrence in a subject in need thereof, comprising administering to the subject an effective amount of any of the oral pharmaceutical compositions disclosed herein.

In one aspect is provided a method of treating and/or preventing hepatic cirrhosis in a subject in need thereof, comprising administering to the subject an effective amount of any of the oral pharmaceutical compositions disclosed herein.

In one aspect is provided a method of treating and/or preventing pouchitis in a subject in need thereof, comprising administering to the subject an effective amount of any of the oral pharmaceutical compositions disclosed herein.

In one aspect is provided a method of treating and/or preventing spontaneous bacterial peritonitis in a subject in need thereof, comprising administering to the subject an effective amount of any of the oral pharmaceutical compositions disclosed herein.

In one aspect is provided a method of treating and/or preventing NAFLD in a subject in need thereof, comprising administering to the subject an effective amount of any of the oral pharmaceutical compositions disclosed herein.

In one aspect is provided a method of treating and/or preventing NAFL in a subject in need thereof, comprising administering to the subject an effective amount of any of the oral pharmaceutical compositions disclosed herein.

In one aspect is provided a method of treating and/or preventing NASH in a subject in need thereof, comprising administering to the subject an effective amount of any of the oral pharmaceutical compositions disclosed herein.

In one aspect is provided any of the methods of treatment disclosed herein, wherein the oral pharmaceutical composition is administered to the subject at a daily dose of 600 mg, 1200 mg or 1800 mg of a pharmaceutically acceptable salt of rifamycin SV. In one aspect are provided any of the oral pharmaceutical compositions disclosed herein, wherein the oral pharmaceutical composition comprises the sodium salt of rifamycin SV and is administered to a subject at a daily dose equivalent to about 582 mg, about 1164 mg or about 1746 mg of rifamycin SV.

In one aspect is provided any of the methods of treatment disclosed herein, wherein the oral pharmaceutical composition is administered to the subject once, twice, three times or multiple times daily.

In one aspect is provided any of the methods of treatment disclosed herein, comprising administering to the subject any of the oral pharmaceutical composition disclosed herein, wherein the oral pharmaceutical composition is administered to the subject three times per day for 1 or more days. In other aspects are provided any of the methods of treatment disclosed herein, comprising administering to the subject any of the oral pharmaceutical composition disclosed herein, wherein the oral pharmaceutical composition is administered to the subject three times per day for 1 or more, or 2 or more, or 3 or more, or 4 or more, or 5 or more, or 6 or more, or 7 or more, or 8 or more, or 9 or more, of 10 or more, or 11, or more, or 12 or more, or 13 or more, of 14 or more, or 15 or more, or 16, or more, or 17 or more, or 18 more, or 19 or more, or 20 or more, or 21 or more, or 22 or more, or 23 or more, or 24 or more, or 25 or more, or 26 or more, or 27 or more, or 28 or more, or 29 or more, or 30 or more days.

In one aspect is provided any of the methods of treatment disclosed herein, comprising administering to the subject any of the oral pharmaceutical composition disclosed herein, wherein the oral pharmaceutical composition is administered to the subject three times per day for 1 day. In other aspects are provided any of the methods of treatment disclosed herein, comprising administering to the subject any of the oral pharmaceutical composition disclosed herein, wherein the oral pharmaceutical composition is administered to the subject three times per day for 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In one aspect is provided a method of treating a subject having IBS-D, comprising administering to the subject an effective amount of any of the oral pharmaceutical compositions disclosed herein, wherein following administration of the oral pharmaceutical composition to the subject, the subject experiences an improvement in the Bristol stool form scale. In other aspects, following administration of an effective amount of any of the oral pharmaceutical compositions disclosed herein, the subject experiences a 20% or greater, a 25% or greater, a 30% or greater, a 40% or greater, a 45% or greater, or 50% or greater, a 55% or greater, a 60% or greater, a 65% or greater, a 70% or greater, a 75% or greater, an 80% or greater, an 85% or greater, a 90% or greater, or a 95% or greater reduction in the number of days per week during which the subject has a stool with a score of 6 or 7 on the Bristol stool form scale.

In one aspect are provided any of the oral pharmaceutical compositions disclosed herein, wherein the rifamycin SV, or a pharmaceutically acceptable salt thereof, is rifamycin sodium.

In one aspect is provided any of the uses or methods disclosed herein, wherein the rifamycin SV, or a pharmaceutically acceptable salt thereof, is rifamycin sodium.

In one aspect are provided any of the oral pharmaceutical compositions disclosed herein comprising rifamycin SV or a pharmaceutically salt thereof, preferably the sodium salt, which are formulated to obtain an extended release profile of the rifamycin SV, or a pharmaceutically acceptable salt thereof.

In one aspect are provided any of the oral pharmaceutical compositions disclosed herein comprising rifamycin SV or a pharmaceutically acceptable salt thereof, preferably the sodium salt, which release the rifamycin SV, or a pharmaceutically acceptable salt thereof, in the small intestine (duodenum, jejunum and ileum).

In one aspect are provided any of the oral pharmaceutical compositions disclosed herein comprising rifamycin SV or a pharmaceutically salt thereof, preferably the sodium salt, which start the release of the rifamycin SV, or a pharmaceutically acceptable salt thereof, in the small intestine (duodenum, jejunum and ileum) and may continue in the large intestine.

In one embodiment, the rifamycin SV, or a pharmaceutically acceptable salt thereof, is released from the composition of the present invention starting after the dissolution and/or breakage of the gastro-resistant coating at the beginning of the proximal part of the intestine, namely the small intestine. In one embodiment of the present invention, the rifamycin SV, or a pharmaceutically acceptable salt thereof, is released from the composition of the present invention solely after the pylorus passage in the proximal part of the intestine, namely small intestine, starting at the dissolution and/or breakage of the gastro-resistant coating. In one embodiment of the present invention, the rifamycin SV, or a pharmaceutically acceptable salt thereof, is released from the composition of the present invention when the composition is exposed to a medium from about pH 5 to about pH 7.5, preferably from about pH 5.5 to about pH 7.0, more preferably from about pH 6.0 to about pH 6.5. In a preferred embodiment, the rifamycin SV, or a pharmaceutically acceptable salt thereof, is released from the composition of the present invention when the composition is exposed to a medium of about pH 6.4. In one embodiment of the present invention, the rifamycin SV, or a pharmaceutically acceptable salt thereof, is released from the composition of the present invention in an amount higher than 80% over a period from about 3 to about 12 hours, preferably over a period of time from 4 to 11 hours, more preferably over a period of time from about 5 hours to about 10 hours, much more preferably from about 5 hours to about 9 hours. In a preferred embodiment, the rifamycin SV, or a pharmaceutically acceptable salt thereof, is released from the composition of the present invention in an amount higher than 80% over a period of about 6 hours. In one embodiment of the present invention, the rifamycin SV, or a pharmaceutically acceptable salt thereof, is released from the composition of the present invention in an amount higher than 80% over a period of about 3 to about 12 hours when exposed to a medium from about pH 5 through about pH 7.5.

In one aspect are provided any of the oral pharmaceutical compositions disclosed herein, wherein the rifamycin SV, or a pharmaceutically acceptable salt thereof, is released from the composition of the present invention starting in the small intestine and optionally continuing in the large intestine.

In one aspect are provided any of the oral pharmaceutical compositions disclosed herein, comprising rifamycin SV or a pharmaceutically salt thereof, preferably the sodium salt, which start the release of the rifamycin SV, or a pharmaceutically acceptable salt thereof, solely after the pylorus passage, in the proximal part of the intestine, after the dissolution and/or breakage of the gastro-resistant coating.

In one aspect are provided any of the oral pharmaceutical compositions disclosed herein comprising rifamycin SV or a pharmaceutically salt thereof, preferably the sodium salt, in which the rifamycin SV, or a pharmaceutically acceptable salt thereof, is released when the composition is exposed to a medium from about pH 5 through about pH 7.5, preferably from about pH 5.5 to about pH 7.0, more preferably from about pH 6.0 to about pH 6.5.

In one aspect are provided any of the oral pharmaceutical compositions disclosed herein, wherein the release of the rifamycin SV, or a pharmaceutically acceptable salt thereof, from the composition begins when the composition is exposed to a medium of about pH 5.5. In another embodiment, the pharmaceutical compositions of the wherein the release of the rifamycin SV, or a pharmaceutically acceptable salt thereof, beings when the composition is exposed to a medium of about pH 6.0. In another embodiment, the pharmaceutical compositions disclosed herein start the release of the rifamycin SV, or a pharmaceutically acceptable salt thereof, when the composition is exposed to a medium of about pH 6.4.

The present invention relates to oral pharmaceutical compositions comprising rifamycin SV or a pharmaceutically salt thereof, preferably the sodium salt, which start the release of the rifamycin SV, or a pharmaceutically acceptable salt thereof, after about 3 hours from the administration of the composition and can continue up to 12 hours. Preferably, the release starts after about 3 hours and continue up to 9 hours.

Suitable salts of the rifamycin SV according to the invention may be selected between sodium or potassium, preferably the sodium salt.

The oral pharmaceutical compositions of the invention are useful for the prevention and/or treatment of cholera and/or SIBO and/or IBS. In particular, the oral pharmaceutical compositions of the invention are useful for the prevention and/or treatment of IBS-C, IBS-D, IBS-M and/or IBS-U; preferably compositions of the invention are useful for the prevention and/or treatment of IBS-D.

Oral pharmaceutical compositions of the invention are also useful for the prevention and/or treatment of diseases or disorders such as hepatic encephalopathy, hepatic cirrhosis, pouchitis, spontaneous bacterial peritonitis, NAFLD, NAFL and/or NASH.

In one embodiment, the oral pharmaceutical compositions according to the present invention, comprise rifamycin SV or a pharmaceutically acceptable salt thereof, at least one lipophilic compound, at least one hydrophilic compound, optionally at least one amphiphilic compound and optionally a gastro-resistant coating.

The dosage of the rifamycin SV, or a pharmaceutically acceptable salt thereof, i.e. rifamycin SV or a pharmaceutically acceptable salt thereof, in the oral pharmaceutical compositions of the invention can be between about 400 mg/dose unit and about 2400 mg/dose unit, between about 400 mg/dose unit and about 2000 mg/dose unit, between about 400 mg/dose unit and about 1500 mg/dose unit, between about 400 mg/dose unit and about 1000 mg/dose unit, between about 400 mg/dose unit and about 800 mg/dose unit, between about 500 mg/dose unit and about 700 mg/dose unit or between about 550 mg/dose unit and about 650 mg/dose unit, preferably about 600 mg of rifamycin SV or a pharmaceutically acceptable salt thereof, in anhydrous form (dried). More preferably, the dosage of the rifamycin SV, or a pharmaceutically acceptable salt thereof, in the oral pharmaceutical composition of the invention is of about 600 mg/dose unit of the rifamycin SV sodium salt in anhydrous form (dried). All the above dosages are to be intended in anhydrous form (dry basis).

In one aspect, when the oral pharmaceutical composition comprises the sodium salt of rifamycin SV (as dry substance), the equivalent amount of rifamycin SV (as a dry substance) in the pharmaceutical composition is between about 388 mg/dose unit and about 2328 mg/dose unit, between about 388 mg/dose unit and about 1940 mg/dose unit, between about 388 mg/dose unit and about 1455 mg/dose unit, between about 388 mg/dose unit and about 960 mg/dose unit, between about 388 mg/dose unit and about 776 mg/dose unit, between about 485 mg/dose unit and about 679 mg/dose unit or between about 533.5 mg/dose unit and about 630.5 mg/dose unit, preferably about 582 mg of rifamycin SV in anhydrous form (dried). More preferably, the dosage of the rifamycin SV, or a pharmaceutically acceptable salt thereof, in the oral pharmaceutical composition of the invention is of about 600 mg/dose unit of the rifamycin SV sodium salt in anhydrous form (dried) which is equivalent to 582 mg/dose unit of rifamycin SV in anhydrous form (dried). All the above dosages are to be intended in anhydrous form (dry basis).

In one embodiment the pharmaceutical compositions of the invention are administered in a daily dose ranging from about 600 mg to about 2400 mg, about 600 mg to about 1800 mg, about 600 mg to about 1200 mg, about 800 mg to about 2400 mg, about 1200 mg to about 2400 mg, or about 1200 mg to about 1800 mg in anhydrous form (dried). In one embodiment, the pharmaceutical compositions of the invention are administered in a daily dose of about 600 mg or about 1200 mg or about 1800 mg in anhydrous form (dried).

In one embodiment, when the oral pharmaceutical composition comprises the sodium salt of rifamycin SV, the equivalent amount of rifamycin SV as a dry substance in the pharmaceutical composition is administered in a daily dose ranges from about 582 mg to about 2328 mg, about 582 mg to about 1746 mg, about 582 mg to about 1146 mg, about 776 mg to about 2328 mg, about 1164 mg to about 2328 mg, or about 1164 mg to about 1746 mg in anhydrous form (dried). In one embodiment, the equivalent amount of rifamycin SV as a dry substance in the pharmaceutical compositions of the invention, such pharmaceutical compositions are administered in a daily dose of about 582 mg or about 1164 mg or about 1746 mg in anhydrous form (dried).

The preferred dosage of the rifamycin SV, or a pharmaceutically acceptable salt thereof, i.e. rifamycin SV or a pharmaceutically acceptable salt thereof, in the oral pharmaceutical compositions of the invention is about 600 mg/dose unit in anhydrous form (dried) or an equivalent of 582 mg /dose unit of rifamycin SV in anhydrous form (dried) when the dosage comprises 600 mg/dose unit of the sodium salt of rifamycin SV in anhydrous form (dried). It is known that the water content is generally of about 12-17% for the rifamycin SV or its salts. According to the present invention we therefore refer to the rifamycin SV or its pharmaceutically acceptable salts in anhydrous form (dried). In order to get one of the dosages of rifamycin SV or a pharmaceutically acceptable salt thereof in anhydrous form hereinabove, the substance to be weighted must be corrected by the water content.

According to an embodiment of the invention, the weight ratio between said at least one lipophilic compound and said at least one hydrophilic compound is between about 1:30 and about 1:90, preferably of about 1:66 or of about 1:67.

According to an embodiment of the invention, the weight ratio between said at least one lipophilic compound and said at least one optional amphiphilic compound is between about 1:1 and about 6:1, preferably of about 3:1.

According to an embodiment of the invention, the weight ratio between said at least one optional amphiphilic compound and said at least one hydrophilic compound and is between about 1:10 and about 1:30, preferably of about 1:20.

According to an embodiment of the invention, the weight ratio between the rifamycin SV, or a pharmaceutically acceptable salt thereof, preferably the sodium salt, and said at least one lipophilic compound is between about 10:1 and about 30:1, preferably of about 20:1.

According to an embodiment of the invention, the weight ratio between the rifamycin SV, or a pharmaceutically acceptable salt thereof, preferably the sodium salt, and said at least one hydrophilic compound is between about 1:1 and about 6:1, preferably of about 3:1.

According to an embodiment of the invention, the weight ratio between the rifamycin SV, or a pharmaceutically acceptable salt thereof, preferably the sodium salt, and said at least one optional amphiphilic compound is between about 30:1 and about 90:1, preferably of about 60:1.

According to an embodiment of the invention, the at least one lipophilic compound may be selected from unsaturated or hydrogenated alcohols (such as cetyl alcohol, stearic alcohol, myristyl alcohol, lauryl alcohol, or oleyl alcohol) or fatty acids, salts, esters thereof (such as such as palmitic, stearic, myristic, lauric, laurylic or oleic acid); fatty acids mono-, di- or triglycerides or polyethoxylated derivatives thereof, such as stearin; waxes, such as beeswax or carnauba wax; ceramides; cholesterol derivatives or mixtures thereof. Stearic acid, or one of its salt (such as, for example, magnesium stearate), is the preferred at least one lipophilic compound. In another embodiment, the lipophilic compound is an ester of a hydrogenated fatty alcohol. In one embodiment, the lipophilic compound is sodium stearyl fumarate. Optionally, the at least one lipophilic compounds has a melting point lower than about 250° C., preferably from about 30 to about 200° C.

According to another embodiment, the at least one hydrophilic compound is represented by generally cross-linked or linear polymeric or copolymeric substances, which are known as hydrogels, that is to say, i.e. substances which when passing from the dry state to the hydrated one, undergo the so-called "molecular relaxation," namely a remarkable increase in mass and weight following the coordination of a large number of water molecules by the polar groups present in their polymeric chains. In particular, the at least one hydrophilic may be selected from cellulose derivatives and their esters and/or salts, such as hydroxyalkylcelluloses (for example hydroxypropylcellulose, hydroxypropylmethylcellulose or sodium hydroxypropylmethylcellulose), alkylcelluloses, carboxyalkylcelluloses (such as sodium carboxymethylcellulose); polyvinyl alcohols; carboxyvinyl derivatives; polysaccharides, such as dextrins, pectins, starches and derivatives thereof; natural or synthetic gums; alginic acid; polyalcohols such as xylitol, maltitol or mannitol. Mannitol or sodium carboxymethylcellulose are the preferred at least one hydrophilic compound; more preferably, they are both contained in the oral pharmaceutical composition of the present invention. For example, the at least one hydrophilic compound may comprise starch or sodium starch glycolate. In one embodiment, the at least one hydrophilic compound comprises starch. In one embodiment, the at least one hydrophilic compound comprises sodium starch glycolate.

According to an embodiment, the compositions of the invention further contain at least one hygroscopic substance. The presence of at least one hygroscopic substance allows to control and/or correct humidity level in the composition itself in order to ensure that the rifamycin SV, or a pharmaceutically acceptable salt thereof, is not damaged following storage and/or exposure to moisture. The at least one hygroscopic substance may be selected from is mannitol, sorbitol, lactose, maltodextrins or a mixture thereof, Preferably, the at least one hygroscopic substance is mannitol.

As above mentioned the rifamycin SV or its salts have a water content of about 12-17% and there is therefore the additional need to maintain or improve the stability of this rifamycin SV, or a pharmaceutically acceptable salt thereof, in the composition itself through the contact with other auxiliaries substances with a lower content of coordinated water.

The control of the water content of the composition, in addition to contribute to the maintenance or improvement of the stability profile of rifamycin SV or its salts in the composition, also ensures the more suitable compression characteristics in case of a tablet, creating an acceptable resistance profile to the mechanical stress of an industrial compression procedure.

The at least one amphiphilic compound, which can be optionally used according to the invention, comprises polar lipids of type I or II (lecithin, phosphatidylcholine, phosphatidylethanolamine), ceramides, glycol alkyl ethers such as diethylene glycol monomethyl ether (Transcutol®), natural or synthetic gums. Lecithin is the preferred at least one amphiphilic compound in the composition.

The oral pharmaceutical composition according to the present invention may also contain at least one physiologically acceptable excipient, for example bioadhesive excipients such as chitosans, polyacrylamides, natural or synthetic gums, acrylic acid polymers and copolymers.

It should be in any case noted that in different environments the above compounds and/or excipients may have a different behaviour.

The oral pharmaceutical composition according to the present invention may be manufactured according to the more general tablets manufacturing process or methods described in WO0076478, which are incorporated herein by reference.

According to an embodiment, the oral pharmaceutical compositions of the invention may be covered with a gastro-resistant coating (film), which may contain polymethacrylates, acrylic and/or methacrylic acids polymers or copolymers or cellulose derivatives, such as cellulose acetophthalate. According to a preferred embodiment, the gastro-protective coating contains polymethacrylates including but not limited to compounds known commercially as Eudragit S100 (methacrylic acid-methyl methacrylate copolymer) 1:2, Eudragit L100 (methacrylic acid-methyl methacrylate 1:1 copolymer) and/or Eudragit L30 D55 (methylacrylic acid-ethylacrylate 1:1 copolymer). According to a preferred embodiment, the gastro-protective coating contains methacrylic acid-methyl methacrylate 1:1 copolymer (Eudragit L100). According to another preferred embodiment, the gastro-protective coating contains methylacrylic acid-ethylacrylate 1:1 copolymer (Eudragit L30 D55). In one embodiment, the gastro-resistant coating (film) may further comprise one or more of talc, triethylcitrate, titanium dioxide, and one or more compounds imparting a color to the oral pharmaceutical composition.

According to an embodiment, the solvent used for the solubilization of the gastro-resistant coating can be organic, aqueous and/or a mixture thereof. The organic solvents may be selected among ethanol, isopropanol, acetone or mixture thereof. Preferably, the organic solvent is ethanol.

It was surprisingly discovered that an aqueous solvent used to obtain the gastro-resistant coating of the invention may ensure an improved stability of the rifamycin SV, or a pharmaceutically acceptable salt thereof, into the pharmaceutical compositions, reducing the formation of impurities of the rifamycin SV, or a pharmaceutically acceptable salt thereof, itself. This was very surprisingly discovered considering the known sensitivity of the rifamycin SV or its salt to the presence of water, and it was unexpected that a stabilization of such an rifamycin SV, or a pharmaceutically acceptable salt thereof, was obtained in the composition of the present invention. In one embodiment the aqueous gastro-resistant coating ensures to have less than about 2.0 wt % of total impurities after 24 months at 25° C. and 60% relative humidity. In another embodiment the aqueous gastro-resistant coating ensures to have less than about 1.5 wt % of total impurities after 24 months at 25° C./60% RH.

In one embodiment the aqueous gastro-resistant coating ensures to have less than about 3.0 wt % of total impurities after 36 months at 25° C. and 60% relative humidity. In another embodiment the aqueous gastro-resistant coating ensures to have less than about 2.5 wt % of total impurities after 36 months at 25° C. and 60% relative humidity. In another embodiment the aqueous gastro-resistant coating ensures to have less than about 2.0 wt % of total impurities after 36 months at 25° C. and 60% relative humidity. The above wt % of total impurities are counted with respect to the amount of rifamycin SV (as labeled claim).

The gastro-resistant coating of the pharmaceutical compositions of the invention may modulate the starting of the release of the rifamycin SV, or a pharmaceutically acceptable salt thereof, from the pharmaceutical compositions of the invention as above disclosed.

According to a further embodiment, the gastro-resistant coating may also optionally comprise at least one plasticizer, at least one dye, or a mixture thereof The oral pharmaceutical composition of the invention may be selected from tablets, capsules, granules and/or microgranules, preferably tablets.

According to an embodiment of the invention, the oral pharmaceutical composition is a tablet, comprising a core and a gastro-resistant coating. In another embodiment, the oral pharmaceutical composition is a table consisting essentially of a core and a gastro-resistant coating. In another embodiment, the oral pharmaceutical composition is a table consisting of a core and a gastro-resistant coating. In one embodiment, the coating covers the core. In another embodiment, the coating is applied directly on or to the core.

In one embodiment, the core is a matrix comprising the ingredients found in the core as described herein. In another embodiment, the core is a mixture comprising the ingredients found in the core as described herein. In one embodiment, the core is a compressed blend comprising the ingredients found in the core as described herein. In one embodiment, the core is a dispersion comprising the ingredients found in the core as described herein.

In one embodiment, the core is a matrix consisting of ingredients in which the ingredients comprise those ingredients described herein. In another embodiment, the core is a mixture consisting of ingredients in which the ingredients comprise those ingredients described herein. In one embodiment, the core is a compressed blend consisting of ingredients in which the ingredients comprise those ingredients described herein. In one embodiment, the core is a dispersion consisting of ingredients in which the ingredients comprise those ingredients described herein.

According to one embodiment, the core may contain sodium rifamycin SV, ascorbic acid, lecithin, stearic acid, sodium carboxymethyl cellulose, mannitol, colloidal anhydrous silica and magnesium stearate; the gastro-resistant coating may contain poly(methacrylic acid-ethylacrilate 1:1—Eudragit L30 D55) or poly(methacrylic acid-methyl methacrylate 1:1—Eudragit L100), one or more dyes (such as titanium dioxide and ferric oxide), talc, triethylcitrate and optionally PEG6000. The gastro-resistant coating may be prepared in aqueous or alcoholic (organic) solutions.

One of the advantages of the oral pharmaceutical composition of the invention is therefore represented by its particular site-specificity with respect to the small intestine. Thank you to the particular composition of the present invention the rifamycin SV, or a pharmaceutically acceptable salt thereof, is in fact released from the composition starting after the dissolution and/or breakage of the gastro-resistant coating at the beginning of the proximal part of the intestine, maximizing the therapeutic effect of the rifamycin SV, or a pharmaceutically acceptable salt thereof, in the portion affected by SIBO and/or IBS and/or cholera.

Another advantage of the oral pharmaceutical composition of the invention is represented by the possibility to obtain an improved stabilization of the rifamycin SV, or a pharmaceutically acceptable salt thereof.

In another embodiment, the oral pharmaceutical compositions of the present invention have a dissolution rate lower than about 10% over about 2 hours when measured at pH 1.

In one embodiment, the oral pharmaceutical compositions of the present invention have a dissolution rate lower than about 20% over about 1 hour, when measured at about pH 6.4.

In one embodiment, the oral pharmaceutical compositions of the present invention have a dissolution rate between about 20% and about 60% over about 3 hours, when measured at about pH 6.4.

In one embodiment, the oral pharmaceutical compositions of the present invention have a dissolution rate of greater than or equal to about 80% of rifamycin SV over about 6 hours, when measured at about pH 6.4.

According to the invention, the dissolutions are measured with the with the USP dissolution apparatus type II equipped with a paddle at 100 rpm at 37°±2° C.

In one embodiment, the oral pharmaceutical compositions of the present invention have a dissolution rate lower than about 20% over about 1 hour, between about 20% and about 60% over about 3 hours and equal or greater than about 80% over about 6 hours, when measured at about pH 6.4 with the USP dissolution apparatus type II equipped with a paddle at 100 rpm at 37°±2° C.

In some embodiments the rifamycin SV, or a pharmaceutically acceptable salt thereof, is thus released solely in the small intestine, so ensuring the complete release of the rifamycin SV or the salt thereof, preferably sodium salt, where it is needed to maximize the treatment and the efficacy.

In some other embodiments the rifamycin SV, or a pharmaceutically acceptable salt thereof, is released starting in the small intestine and continuing within the large intestine.

The oral pharmaceutical compositions of the invention are particularly useful for the prevention and/or treatment of SIBO and/or IBS, because they downregulate the bacterial overgrowth to a normal growing level.

The oral pharmaceutical compositions of the invention are particularly useful for the prevention and/or treatment of cholera.

In one embodiment, the present invention is therefore a method for preventing and/or treating SIBO, IBS and/or cholera comprising administering an oral pharmaceutical composition of the present invention as above described to a subject in need thereof, preferably a human subject.

In one embodiment, the present invention is a method of preventing and/or treating IBS-C, IBS-D, IBS-M and/or IBS-U; preferably the treatment of IBS-D comprising administering an oral pharmaceutical composition of the present invention to a subject in need thereof, preferably a human subject.

In another embodiment, the present invention is a method of treating cholera comprising administering an oral pharmaceutical composition of the present invention to a subject in need thereof, preferably a human subject.

In another embodiment, the present invention is a method of treating and/or preventing hepatic encephalopathy, hepatic cirrhosis, pouchitis and/or spontaneous bacterial perotinitis comprising administering an oral pharmaceutical composition of the present invention to a subject in need thereof, preferably a human subject.

In another embodiment, the present invention is a method of treating and/or preventing NAFLD, NAFL and/or NASH comprising administering an oral pharmaceutical composition of the present invention to a subject in need thereof, preferably a human subject.

The oral pharmaceutical compositions of the invention preferably contain about 600 mg/dose unit of the rifamycin SV, or a pharmaceutically acceptable salt thereof, in anhydrous form (i.e. rifamycin SV or a pharmaceutically acceptable salt thereof, preferably rifamycin SV sodium salt). When the oral pharmaceutical compositions of the invention contain 600 mg/dose unit of the sodium salt of rifamycin SV in anhydrous form, the equivalent amount of rifamycin SV in anhydrous form is 582 mg/dose unit.

In one embodiment, the compositions are preferably administered according to a dose regimen of three tablets a day (i.e. t.i.d., ter in die or all together once in a day), in order to reach the optimal daily dosage of about 1800 mg/day. Said t.i.d. daily dose regimen preferably lasts 14 days, but could be protracted for several months.

In another embodiment, the oral pharmaceutical composition of the inventions are preferably administered according to a dose regimen of two tablets a day (i.e. b.i.d., bis in die or all together once in a day), in order to reach the optimal daily dosage of about 1200 mg/day. Said b.i.d. daily dose regimens preferably lasts for a period of 1-4 weeks, preferably for 14 days, but could be protracted for several months.

The following experimental section describes the invention in detail without limiting the content thereof in any way.

EXAMPLES

Example 1

Rifamycin sodium 600 mg extended-release coated tablets having the quali-quantitative composition disclosed in Table 1 were manufactured.

Organic Film Coated (Gastro-Resistant Coating)

TABLE 1

| Ingredients | Unit | Amount per tablet |
|---|---|---|
| Core composition | | |
| Rifamycin SV sodium[1] | mg | 600[1] |
| Ascorbic acid | mg | 30.0 |
| Lecithin | mg | 10.0 |
| Stearic acid | mg | 30.0 |
| Sodium carboxymethyl cellulose (Na CMC) | mg | 200.0 |
| Mannitol | mg | 215.0[2] |
| Colloidal anhydrous silica | mg | 20.0 |
| Magnesium stearate | mg | 25.0 |
| Coating composition | | |
| Methacrylic Acid - Methyl Methacrylate Copolymer (1:1) (Eudragit ® L100) | mg | 41.0 |
| Titanium dioxide | mg | 11.0 |
| Red ferric oxide | mg | 0.6 |
| Talc | mg | 18.2 |
| Triethylcitrate | mg | 8.2 |
| Polyethylene glycol 6000 | mg | 1.0 |
| Ethanol[3] | — | — |
| Purified water[3] | — | — |

[1]as anhydrous substance (dried), being equivalent to about 702 mg of rifamycin SV sodium salt in hydrated form considering a mean water content of about 14.5%.
[2]mannitol amount is adjusted to compensate for rifamycin SV sodium amount correction based on water content.
[3]Purified water and ethanol are essentially removed during manufacturing process.

Rifamycin SV (sodium salt), ascorbic acid, lecithin, stearic acid and a portion of magnesium stearate were mixed in a suitable container till homogeneity of dispersion was obtained. Then mannitol, sodium carboxymethyl cellulose and silica were added and the mixture was mixed again; the addition of magnesium stearate was completed, and the powder was compressed into a rotating tableting machine to obtain the tablet cores. These latter were then coated in a pan coat unit with Eudragit L100, triethylcitrate, talc, titanium dioxide and red ferric dioxide using ethanol as solvent to apply the gastro-resistant coating layer. The tablets were then polished by adding some polyethylene glycol 6000 in a water solution.

The tablets prepared were evaluated in a dissolution test at pH1 under the conditions in Table 2:

TABLE 2

| Instrumentation | USP dissolution apparatus II complying with USP <711>; UV-Visible spectrophotometer connected to a PC for data recording |
|---|---|
| Stirrer speed | 50 rpm |
| Medium | HCl 0.1M + 0.4% Macrogol Cetostearyl Ether |
| Volume | 1000 mL |
| Medium temperature | 37 ± 0.5° C. |
| Testing period | 2 hours |
| Wavelength | 299 nm |
| Quartz glass cell | 0.1 cm |

The dissolution testing was carried by transferring 1000 mL of pH 1 dissolution medium to the test vessel and warming the solution to 37° C.±0.5° C. One tablet of the composition was added to the test vessel. After 2 hours, the dissolution medium of each vessel was sampled, filtered and analyzed versus a blank containing the dissolution medium using a UV-visible spectrophotometer.

At the end of the dissolution period (2 hours), the dissolution medium of each vessel will be sampled, filtered and analysed versus the blank using the UV-Visible spectrophotometer. The amount of rifamycin SV sodium released from the tablet in the test vessel was calculated using the formula:

$$(\%) \text{ Rifamycin sodium } SV \text{ dissolved amount} = \frac{A_c \times R_f \times 1000}{600} \times 100$$

where:
$A_c$=Absorbance of sample solution;
$R_f$=Response factor of the calibration curve (concentration mg/mL vs absorbance of standard solutions);
900=Dissolution volume (mL);
600=Rifamycin sodium SV theoretical amount (mg/tablet).

The amount of rifamycin SV released from the tablets manufactured according to Example 1 in the dissolution test at pH 1 are disclosed in Table 3:

TABLE 3

| Time | Amount rifamycin SV released from tablet in a pH 1 dissolution medium (% total amount of rifamycin SV sodium contained in tablet tested) |
|---|---|
| 2 hours | ND* |

*ND = not detected within the limits of detection of the analytical method utilized.

The tablets prepared were also evaluated in a dissolution test at pH 6.4 under the conditions in Table 4.

TABLE 4

| Instrumentation | USP dissolution apparatus II complying with USP <711>; UV-Visible spectrophotometer connected to a PC for data recording |
|---|---|
| Stirrer speed | 100 rpm |
| Medium | Buffer pH 6.4 USP |

TABLE 4-continued

| Instrumentation | USP dissolution apparatus II complying with USP <711>; UV-Visible spectrophotometer connected to a PC for data recording |
|---|---|
| Volume | 900 mL |
| Medium temperature | 37 ± 0.5° C. |
| Testing period | 6 hours in Buffer pH 6.4 USP |
| Wavelength | 314 nm |
| Quartz glass cell | 0.1 cm |

The test solution was prepared by dissolving 6.8 g of monobasic potassium phosphate ($KH_2PO_4$) and 0.5 g of NaOH in about 400 mL of purified water and diluting to a total volume of 1000 mL with purified water. The standard solution for use in the analytical procedure was prepared as a solution of 0.67 mg/mL Rifamycin SV W.S. in the dissolution medium.

The dissolution testing was carried by transferring 900 mL of pH 6.4 buffer to the test vessel and warming the solution to 37° C.±0.5° C. One tablet of the composition was added to the test vessel. At the pre-determined sampling times, the dissolution medium of each vessel was sampled, filtered and analyzed versus a blank containing the dissolution medium using a UV-visible spectrophotometer. The amount of rifamycin SV sodium released from the tablet in the test vessel was calculated using the formula:

$$(\%) \text{ Rifamycin sodium } SV \text{ dissolved amount} = \frac{A_c \times R_f \times 900}{600} \times 100$$

Where:
$A_c$=Absorbance of sample solution;
$R_f$=Response factor of the calibration curve (concentration mg/mL vs absorbance of standard solutions);
900=Dissolution volume (mL);
600=Rifamycin sodium SV theoretical amount (mg/tablet).

The amounts of rifamycin SV released from the tablets manufactured according to Example 1 in the dissolution test at pH 6.4 are disclosed in Table 5.

TABLE 5

| Time | Amount rifamycin SV released from tablet in a pH 6.4 dissolution medium (% total amount of rifamycin SV sodium contained in tablet tested) |
|---|---|
| 1 hour | 2% |
| 2 hours | 13% |
| 3 hours | 37% |
| 4 hours | 58% |
| 6 hours | >80% (95%, 96% and 94% based on testing of three tablets) |

Stability: a stability study was carried on one batch of the tablets manufactured according to Example 1 according to the ICH Guideline on stability studies of new drug products. The tablets were placed at 25° C./60% RH. The results are reported in below Table 5a.

TABLE 5a

| Time point | Assay (mg/tablet) | Assay (% of labeled claim) | Rifamycin S (%) | Any other related substances (%) | Total related substances (%) |
|---|---|---|---|---|---|
| 0 | 592.0 | 98.7 | <0.02 | 0.09 | 0.32 |
| 6 months | 576.3 | 96.1 | 0.06 | 0.24 | 0.71 |

TABLE 5a-continued

| Time point | Assay (mg/ tablet) | Assay (% of labeled claim) | Rifamycin S (%) | Any other related substances (%) | Total related substances (%) |
|---|---|---|---|---|---|
| 12 months | 579.6 | 96.6 | 0.07 | 0.28 | 1.23 |
| 24 months | 574.2 | 95.7 | 0.07 | 0.35 | 1.68 |
| 36 months | 574.0 | 95.7 | 0.11 | 0.33 | 2.02 |

Example 2

Rifamycin sodium 600 mg extended-release coated tablets having the quali-quantitative composition disclosed in Table 6 were manufactured.

Aqueous Film Coated (Gastro-Resistant Coating):

TABLE 6

| Ingredients | Unit | Amount per tablet |
|---|---|---|
| Core composition | | |
| Rifamycin SV sodium[(1)] | mg | 600.0[(1)] |
| Ascorbic acid | mg | 30.0 |
| Lecithin | mg | 10.0 |
| Stearic acid | mg | 30.0 |
| Sodium carboxymethyl cellulose (Na CMC) | mg | 200.0 |
| Mannitol[2] | mg | 215.0[2] |
| Colloidal anhydrous silica | mg | 20.0 |
| Magnesium stearate | mg | 25.0 |
| Coating composition | | |
| Poly(methacrylic acid-ethyl acrylate (1:1)) (Eudragit ® L30 D55) | mg | 49.8[3] |
| Titanium dioxide | mg | 2.7 |
| Red ferric oxide | mg | 0.2 |
| Talc | mg | 22.2 |
| Triethylcitrate | mg | 5.1 |
| Purified water[4] | — | — |

[(1)]as anhydrous substance (dried), being equivalent to about 702 mg of rifamycin SV sodium salt in hydrated form, considering a mean water content of about 14.5%.
[2]mannitol amount is adjusted to compensate for rifamycin SV sodium amount correction based on water content.
[3]In anhydrous form.
[4]Purified water is essentially removed during manufacturing process.

Stability: a stability study was carried on one batch of the tablets manufactured according to Example 2 according to the ICH Guideline on stability studies of new drug products. The tablets were placed at 25° C./60% RH. The results are reported in below Table 6a.

TABLE 6a

| Time point | Assay (mg/ tablet) | Assay (% of labeled claim) | Rifamycin S (%) | Any other related substances (%) | Total related substances (%) |
|---|---|---|---|---|---|
| 0 | 592.7 | 98.8 | 0.08 | 0.09 | 0.45 |
| 6 months | 590.0 | 98.3 | 0.09 | 0.19 | 0.73 |
| 12 months | 586.9 | 97.8 | 0.06 | 0.25 | 1.12 |
| 24 months | 588.4 | 98.1 | 0.05 | 0.29 | 1.22 |
| 36 months | 583.3 | 97.2 | 0.10 | 0.36 | 1.48 |

Example 3

In Vitro Characterization of Anti-Inflammatory Properties of Rifamycin SV

Inflammation plays a major role in the pathogenesis of IBS, for this reason rifamycin SV capability to inhibit inflammation was characterized. Characterization by PXR stimulation and NFkB inhibition was performed in vitro in cell systems mimicking the gut environment in the context of IBS.

Assay to analyze and quantitate PXR activity:

A nuclear receptor assay system which utilizes proprietary human cells engineered to provide constitutive, high-level expression of the human PXR, was used to determine the EC50 of rifamycin SV agonist activity on the PXR.

This assay product from Indigo Biosciences (Pennsylvania, USA) utilizes cells that express a hybrid form of human PXR. The N-terminal sequence encoding the PXR DNA binding domain (DBD) was substituted with that of the yeast GAL4-DBD. The native PXR ligand binding domain (LBD) and other C-terminal domains remain intact and functional. Ligand interaction activates the receptor, causing it to bind to the GAL4 DNA binding sequence, which is functionally linked to a resident luciferase reporter gene. Thus, quantifying changes in luciferase activity in the treated reporter cells provides a sensitive surrogate measure of the changes in PXR activity. The principle application of this reporter assay system is in the screening of test samples to quantify any functional activity, either agonist or antagonist, that they may exert against human PXR. Increasing concentration of rifamycin SV were tested in comparison with rifaximin, Rifampicin was used as positive control for the assay. Experiments were repeated 3 times and standard deviation calculated. The EC50 and 95% CI were determined using Prism statistical analysis software, fitting a nonlinear curve through the data points expressed as log(agonist) vs. response—variable slope (4 parameters). The p value was calculated using Prism parametric, paired t test analysis.

Assay to measure NFkB activity:

The assay to determine the IC50 of rifamycin SV antagonism of the NFkB transcription factor used a similar reporter system as the PXR assay. The NFkB nuclear receptor assay system from Indigo Biosciences utilizes human kidney epithelial cells transiently transfected with an NF-kB reporter. The NFkB biologic activity measured as transcriptional activity from these reporter cells demands the same orchestration of all intracellular molecular interactions and events that can be expected to occur in vivo.

Cells were treated under antagonist mode in the presence of 30 ng/mL TNFα to stimulate the NFkB inflammatory cascade. Increasing concentration of rifamycin SV were tested in comparison with rifaximin. After 24 hours, luminescence which is proportional to NFkB transcriptional activity was quantitated. Experiments were repeated 2 times and standard deviation calculated. The IC50 and 95% CI were determined using Prism statistical analysis software, fitting a nonlinear curve through the data points expressed as log(inhibitor) vs. response (3-parameter). The p value was calculated using Prism parametric, paired t test analysis.

Experimental results showed that rifamycin SV is 200-440 times more potent than rifaximin at stimulating PXR transcriptional activity. Additionally, rifamycin SV is also 4000 times more potent than rifaximin at inhibiting NFkB transcriptional activity.

All the presented data, show that rifamycin SV is endowed with a potent anti-inflammatory activity that is far superior to rifaximin. These characteristic make rifamycin SV a very good candidate for IBS treatment and an ideal substrate for a formulation intended to be indicated for the relief of the symptoms of the IBS, particularly the IBS-D. Of course, in order to be an effective tool for the patient healing, the rifamycin SV, or a pharmaceutically acceptable salt thereof, has to be administered at the right dose and with the ideal delivery rate and extent, as ensured by the previous examples that are devoted to ensure that the right amount of rifamycin SV, or a pharmaceutically acceptable salt thereof, be administered to the patients and delivered in the organs where it could display the proper pharmacodynamic activity.

Example 4

Pharmacokinetics and Safety Assessment

The tablets of Example 1 (Rifamycin SV sodium 600 mg tablets) were tested in male and female healthy volunteers to evaluate the safety of the administration and the PK profile obtained after single dose (at day 1) and multiple dose (after 7 days) administration of Rifamycin SV of the invention tablets TID for a cumulative daily intake of 1800 mg/day.

The primary end-point of the study was the evaluation of the pharmacokinetics of rifamycin SV in plasma and urine after single (Day 1) and multiple doses (Day 7) of the tablets of Example 1 administered to healthy subjects according to a 600 mg t.i.d. (ter in die) dose regimen.

The secondary end point of the study was the evaluation of safety and tolerability of the tablets of Example 1 administered according to a t.i.d. dose regimen for 14 consecutive days. All the study subjects received the tablets of Example 1 according to a multiple dose regimen from Day 1 to Day 14 as follows:

1800 mg of sodium rifamycin SV as one 600 mg tablet of Example 1 3 times a day (t.i.d.) for 7 consecutive days, at 08:00±1 h (before breakfast), 14:00±1 h (before lunch) and 20:00±1 h (before dinner). Between the 1st and the 2nd and between the 2nd and the 3rd dose τ=6 h on each treatment day. Between the 3rd dose of one day and the 1st dose of the following day τ=12 h.

after discharge on Day 8, the subjects continued the treatment according to the same dose regimen at home up to Day 14 for a total of 42 administrations.

The pharmacokinetics criteria for evaluation were the following:

$C_{max,0-6}$, $t_{max,0-6}$, $AUC_{0-6}$, $AUC_{0-\infty}$, $t^{1/2}$, $\lambda_z$, $Cl/F$, $Cl_r$ and $V_z/F$ of plasma rifamycin SV after the first dose of tablets of Example 4;

$C_{max,0-24}$, $t_{max,0-24}$ and $AUC_{0-24}$ of plasma rifamycin SV after the first 3 doses of Rifamycin SV 600 mg tablets;

$C_{max,ss,12-18}$, $t_{max,ss,12-18}$, $C_{min,ss,12-18}$, $C_{ave,12-18}$, PTF $\%_{12-18}$ and $AUC_{ss,12-18}$ of plasma rifamycin SV after the last multiple dose of Rifamycin SV 600 mg tablets;

$AUC_{ss,0-24}$ of plasma rifamycin SV after the last 3 doses of Rifamycin SV 600 mg tablets; and $Ae_{0-24}$ and % $Ae_{0-24}$ of urinary rifamycin SV after the 3 first and the 3 last multiple doses of Rifamycin SV 600 mg tablets.

Pharmacokinetic parameters and results:

Mean (+SD) Rifamycin SV concentration (ng/mL) vs. time profiles at Day 1 and Day 7 during study treatment with the test formulation are shown in FIG. 1.

Pharmacokinetic parameters of plasma rifamycin SV measured and calculated on days 1 and 7 of the treatment are shown below; mean±SD is reported (N=18) except for $t_{max}$ for which median (range) are shown in Table 7.

TABLE 7

| Parameter | Unit | Day 1 | Parameter | Unit | Day 7 |
|---|---|---|---|---|---|
| $C_{max,\ 0-6}$ | ng/mL | 2.19 ± 1.94 | $C_{max,\ ss12-18}$ | ng/mL | 2.90 ± 1.73 |
| $t_{max,\ 0-6}$ | h | 6.00 (4.00-6.00) | $t_{max,\ ss12-18}$ | h | 12.00 (12.00-18.00) |
| $AUC_{0-6}$ | (ng)(h)/mL | 3.26 ± 2.85 | $C_{min,\ ss12-18}$ | ng/mL | 1.55 ± 0.39 |
| $C_{max,\ 0-24}$ | ng/mL | 5.79 ± 4.24 | $C_{average,\ 12-18}$ | ng/mL | 2.02 ± 0.66 |
| $t_{max,\ 0-24}$ | h | 9.50 (4.00-24.00) | $AUC_{ss,\ 12-18}$ | (ng)(h)/mL | 12.15 ± 3.95 |
| $AUC_{0-24}$ | (ng)(h)/mL | 43.67 ± 20.15 | PTF $\%_{12-18}$ | % | 59.70 ± 42.48 |
|  |  |  | $AUC_{ss,\ 0-24}$ | (ng)(h)/mL | 80.08 ± 34.09 |

$C_{max,0-6}$ corresponds to the "peak concentration," i.e. the peak plasma concentration of a drug in a period of 0-6 h after oral administration and $t_{max,0-6}$ corresponds to "time to peak concentration," i.e. the time to reach the peak plasma concentration in a period of 0-6 h after oral administration of a drug after oral administration.

$C_{max,0-24}$ corresponds to the "peak concentration," i.e. the peak plasma concentration of a drug in a period of 0-24 h after oral administration and $t_{max,0-24}$ corresponds to "time to peak concentration," i.e. the time to reach the peak plasma concentration in a period of 0-24 h after oral administration of a drug after oral administration.

AUC, which corresponds to "area under curve". i.e. the integral of the concentration-time curve (after a single dose or in steady state). In particular, AUC0-6 is the area under the curve up to 6 h, AUC0-24 is the area under the curve up to 24 h, and AUC0-∞ is the area under the curve up to infinity.

The total amount of rifamycin SV excreted in urine calculated on days 1 and 7 of the treatment is reported in Table 8 below (Mean±SD is reported)

TABLE 8

| $Ae_{0-24}$ | ng | 27173.3359 ± 16935.3754 | $Ae_{0-24}$ | ng | 59628.8089 ± 24946.1413 |
|---|---|---|---|---|---|
| % $Ae_{0-24}$ | % | 0.0015 ± 0.0009 | % $Ae_{0-24}$ | % | 0.0033 ± 0.0014 |

Safety results:

No severe AEs were reported, and no subject discontinued the study due to AEs. No significant change in vital signs, BW, ECGs or laboratory parameters was observed after treatment with rifamycin SV. No significant change in liver or kidney functions was observed during the multiple doses treatment.

Conclusions:

The PK profile and the safety of systemically available rifamycin SV after single and multiple t.i.d. doses of rifamycin SV 600 mg tablets were investigated in 18 healthy male and female subjects. The subjects were exposed to a daily dose of 1800 mg of rifamycin SV for 14 consecutive days for the first time. PK of rifamycin SV was investigated in plasma and in urine on days 1 and 7. On day 1, rifamycin SV was quantifiable in plasma levels in all the subjects starting from 9 h after the $1^{st}$ dose. On average, rifamycin SV attained a peak in a median time of 9.5 h ($C_{max,0-24}$: 6.23±4.52 ng/mL). On day 7, all the subjects had quantifiable levels of rifamycin SV in plasma at each sampling time. Rifamycin SV attained a peak 2 h after the $1^{st}$ dose of day 7 and afterwards decreased to levels meanly similar to those of day 1. After 7 days of t.i.d. treatment, the absorption of rifamycin SV slightly increased in rate and extent and did not show any remarkable sign of accumulation. The total amount of rifamycin SV excreted in urine was 0.0033% on day 7.

Rifamycin SV 600 mg tablets showed an excellent safety profile.

Example 5

Activity of Rifamycin SV Against Bacterial Strains

The efficacy of rifamycin SV and its salt in the treatment of SIBO and/or IBS has been verified by evaluation of the MIC (Minimum Inhibiting Concentration) on a specific pathogenic bacterial strain, i.e. *Methanobrevibacter smithii*, which is usually present in IBS patients, especially IBS-D patients, compared with other antibacterial agents, as shown in Table 9.

TABLE 9

| MIC | *Methanobrevibacter smithii* (DSMZ 11975) |
|---|---|
| Rifamycin SV sodium (batch n.: QRM0030) | <1 µg/mL |
| Rifaximin (batch n.: TF10106) | 25 µg/mL |
| Neomycin (Code: N0401000 batch. 4.0) | >100 µg/mL |
| Metronidazole (Code M3761 batch. 095K0693) | 25 µg/mL |

As it shall be appreciated, rifamycin SV is more effective than the other active agents which have been already described as suitable for the SIBO and/or IBS treatment.

The activity of rifamycin SV in an assay of agonism of PXR transcriptional activity, in comparison to the activity of rifaximin and rifampicin, is presented in Table 10.

TABLE 10

| Tested Compound | Agonism of PXR transcriptional activity expressed as EC50 Molar (95% CI range) |
|---|---|
| Rifamycin SV | 6.08E−09 (values in the nM range) |
| Rifaximin | 1.8E−06 (values in the µM range) |
| Rifampicin (assay positive control) | 1.1E−06 (values in the µM range) |

Based on EC50 values of agonist activity on PXR transcriptional potency, rifamycin SV is 200-440 times more potent than rifaximin and rifampicin. The difference in potency between rifaximin and rifamycin SV in this assay was determined to be statistically significant, having a p value of 0.018. Rifaximin at 30 µM is 2.5 times less potent than rifamycin SV at 0.3 µM. This translates to rifamycin SV being 250 times more potent than rifaximin in stimulating PXR transcriptional activity. Thus, rifamycin SV is confirmed to be effective in inflammatory intestinal diseases and more potent in stimulating PXR activity: in facts, using an expected dose 100 times lower. Rifamycin SV is shown also to be 180 times more potent than rifampicin, used in the experimental assay as positive control.

Example 6A

Activity of Rifamycin and Rifaximin in an NFkB Agonism Assay

The agonism of NFkB agonism of rifamycin SV and rifaximin were tested in an assay. The results are shown in the Table 11.

TABLE 11

| Tested Compound | Antagonism of NFkB activity IC50 Molar (95% CI range) |
|---|---|
| Rifamycin SV | 2.3E−08 = 23 nM |
| Rifaximin | 8.3E−05 = 83 µM |

Example 6B

Inhibition of NFkB Transcriptional Activity in a Reporter Cell Line

Figure 4A:
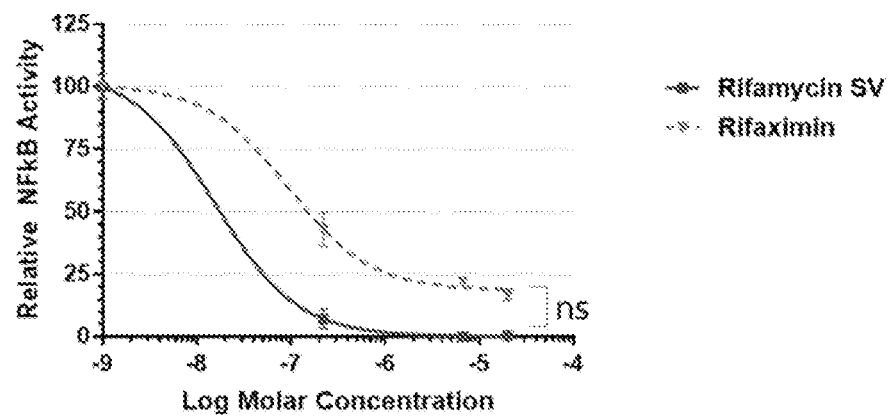
FIGS. 4A-4C: Shows rifamycin SV (■), rifaximin (▼) or rifampicin (●) inhibition of NFkB transcriptional activity induced by PMA (4A), TNFα (4B) or LPS (4C) in a NFkB reporter cell line.
Figure 4B:
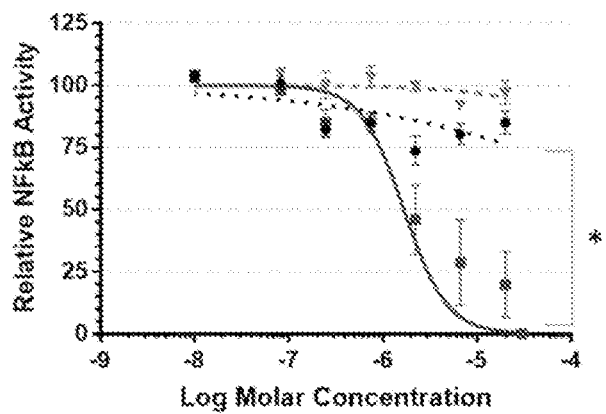
Figure 4C:
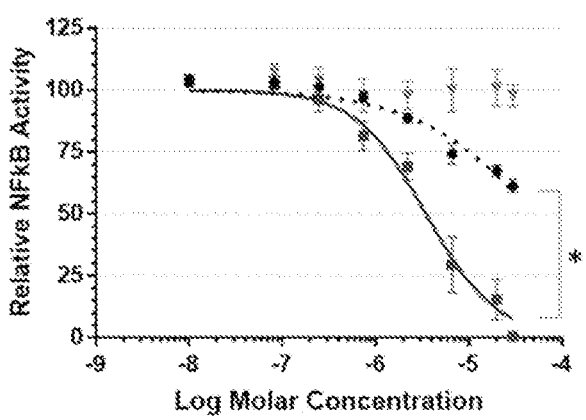

To establish that NFκB inhibition occurs upon rifamycin-induced PXR activation, a reporter cell line expressing full length NFκB and harboring luciferase reporter gene functionally linked to upstream NFκB genetic response elements, was stimulated with either PMA, TNFα or LPS to induce NFκB. Rifamycin or rifaximin were dose-titrated onto these stimulated cells. After 24 hr incubation, luminescence correlating to NFκB transcriptional activity was quantified. Rifamycin was more potent than rifaximin in antagonizing PMA-induced NFκB activity with $IC_{50}$ values of $1.56 \times 10^{-8}$ M vs. $9.39 \times 10^{-8}$ M, respectively, representing a 6 times higher potency than rifaximin (FIG. 4A). Rifamycin also antagonized TNFα-induced NFκB activity with $IC_{50}$ value of $1.48 \times 10^{-5}$ M (FIG. 4B) and LPS-induced NFκB activity with $IC_{50}$ value of $3.49 \times 10^{-6}$ M (FIG. 4C). In stark contrast, rifaximin did not inhibit TNFα- nor LPS-induced NFκB activity up to the highest concentration tested. These results establish a convincing correlation between PXR activation and NFκB inhibition by rifamycin, regardless of the inflammation stimulus.

Since PXR can indirectly regulate inflammation through inhibition of NFκB, the data show that rifamycin induces an alternate or parallel pathway to normalize gut immune function via antagonism of NFκB activity. Rifamycin exhibited strong antagonism of PMA, TNFα, and LPS-induced NFκB activity. PMA by-passes induction of NFκB that is mediated via cell surface receptors by directly activating protein kinase C. Thus, antagonism of PMA-induced NFκB is an indicator of potential inhibition of signaling from multiple cell surface receptors. Rifamycin was more potent than rifaximin in antagonizing PMA-induced NFκB. When the TNFα receptor was specifically activated to stimulate NFκB, rifamycin potently antagonized TNFα-induced signaling while rifaximin was ineffective. More importantly, there was robust inhibition by rifamycin of LPS-induced NFκB, while rifaximin was ineffective.

Interestingly, these data show that inhibition of NFκB by rifamycin is not dependent on the stimulus since rifamycin potently inhibited PMA, TNFα, and LPS-induced NFκB, in contrast to rifaximin, which only inhibited PMA-induced NFκB. PMA or diacyl glycerol-activated PKC is important for T cell receptor or IgE-induced NFκB that occurs in immune cells, like T cells and mast cells, respectively. On the other hand, TNF or LPS-induced NFκB that occurs in colonic epithelial cells requires other signaling factors (TRAFs, TNFR-associated factors). Most importantly, for its relevance in IBS or IBD, NFκB biologic function was confirmed in colonic epithelial cells. Rifamycin significantly inhibited IL1β-induced synthesis of an NFκB-regulated chemokine, IL-8. These cell-dependent requirements for inducing inflammation imply that by acting on various target cells, rifamycin's anti-inflammatory potential is broad because dysregulated immune and epithelial cell interactions contribute to the pathogenesis of several GI disorders.

Example 7

A Phase II, multicenter, randomized, double-blind, placebo controlled, proof of concept study of efficacy and safety of the 600 mg tablets of Example 1 in subjects having with diarrhea-predominant irritable bowel syndrome (IBS-D).

Subjects suffering from IBS-D will be randomly assigned (1:1:1) to one of three treatment groups and will receive one of the following treatments for 14 consecutive days:

☐ Treatment group 1:

The tablets of Example 1 will be administered three times daily (t.i.d.) to the subject according to the following schedule: (a) one 600 mg tablet in the morning; (b) one 600 mg tablet in the afternoon; and (c) one 600 mg tablet in the evening.

☐ Treatment group 2:

The tablets of Example 1, will be administered two times daily (b.i.d.), plus a matching placebo daily (q.d.) to the subject according to the following schedule: (a) one 600 mg tablet in the morning; (b) a placebo tablet in the afternoon; and (c) one 600 mg tablet in the evening.

☐ Treatment group 3:

Placebo tablets will be administered three times daily (t.i.d.) to the subject according to the following schedule: (a) one placebo tablet in the morning; (b) one placebo tablet in the afternoon; and (c) one placebo tablet in the evening.

All the subjects will take the assigned tablets t.i.d., ideally at the following times: 07:30±2 h, 15:30±2 h and 23:30±2 h, for 14 days. The treatment weeks will be followed by ten (10) follow-up weeks.

The primary end-point of the study will be the proportion of weekly responders defined as subjects who weekly have relief of the composite of abdominal pain and stool consistency, on the basis of their daily assessments. Relief of abdominal pain is defined as a decrease in the weekly average of abdominal pain score of at least 30% compared with baseline and relief of stool consistency is defined as a 50% or greater reduction in the number of days per week with at least one stool that has a consistency of Type 6 or 7 compared with baseline 7 according to the 7-point Bristol stool form scale.

The Bristol stool scale is a graded visual scale of stool density. It is validated as a proxy for gastrointestinal transit times and used to define "diarrhea" by the European Society for Clinical Microbiology and Infectious Disease for Clostridium difficile infection (CDI). The parameters of the scale are described in Table 12.

Subjects administered the 600 mg tablets of Example 1 twice or three times a day according to the schedule above will observe relief of abdominal pain measured as a decrease in the weekly average of abdominal pain score of at least 30% compared with baseline and relief of stool consistency measured as a 50% or greater reduction in the number of days per week with at least one stool that has a consistency of Type 6 or 7 compared with baseline 7 according to the 7-point Bristol stool form scale.

TABLE 12

| Score | Description |
| --- | --- |
| 1 | Separate hard lumps, like nuts |
| 2 | Sausage-shaped but lumpy |
| 3 | Like a sausage but with cracks on the surface |
| 4 | Like a sausage or snake, smooth and soft |
| 5 | Soft blobs with clear-cut edges |
| 6 | Fluffy pieces with ragged edges, a mushy stool |
| 7 | Watery, no solid pieces, entirely liquid |

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. An oral pharmaceutical composition in the form of a solid dosage form comprising 540-660 mg of rifamycin SV, or a pharmaceutically acceptable salt thereof, and one or more pharmaceutically acceptable excipients,
    wherein the oral pharmaceutical composition further comprises:
        (a) one or more lipophilic compounds selected from the group consisting of (i) unsaturated or hydrogenated alcohol, (ii) fatty acid, salt, or ester thereof, (iii) fatty acid mono-, di- or triglyceride or polyethoxylated derivative thereof, (iv) wax, (v)ceramide, (vi) cholesterol derivative or mixture thereof, (b) one or more hydrophilic compounds, and (c) one or more amphiphilic compound; and a gastro-resistant coating comprising a polymer selected from the group consisting of methacrylic acid-methyl methacrylate copolymer 1:2, methacrylic acid methyl methacrylate 1:1 copolymer, and methylacrylic acid-ethyl-acrylate 1:1 copolymer, and
    wherein the pharmaceutical composition is formulated for modified release, wherein the solid dosage form comprises a core and the gastro-resistant coating covering the core, wherein the pharmaceutical composition releases not less than about 50% of the amount of rifamycin SV, or a pharmaceutically acceptable salt thereof, comprising the pharmaceutical composition when the pharmaceutical composition is placed in a USP dissolution apparatus II complying with USP <711> for 6 hours, wherein the dissolution apparatus comprises 900 mL of an aqueous buffer at pH 6.4 and at a temperature of 37±0.5° C., and wherein the aqueous solution is stirred at a rate of 100 rpm, and wherein the oral pharmaceutical composition releases the rifamycin SV, or a pharmaceutically acceptable salt thereof, when the solid dosage form is placed in an aqueous medium having a pH in the range of about pH 5 to about pH 6.5.

2. The oral pharmaceutical composition according to claim 1, wherein the oral pharmaceutical composition is formulated to release the rifamycin SV, or a pharmaceutically acceptable salt thereof, in the small intestine, or following passage of the solid dosage form into the pylorus passage in the proximal part of the intestine.

3. The oral pharmaceutical composition according to claim 1, wherein the administration of one or more of the solid dosage forms to a subject exhibits a $t_{max,0-24}$ of the rifamycin SV in the plasma of the subject of about 9.50 hours.

4. The oral pharmaceutical composition according to claim 1, wherein the administration of three or more of the solid dosage forms to a subject exhibits a $C_{max,0-24}$ of the rifamycin SV in the plasma of the subject of about 6.23±4.52 ng/mL.

5. The oral pharmaceutical composition according to claim 1, wherein the administration of three or more of the solid dosage forms to a subject exhibits an $AUC_{0-24}$ of the rifamycin SV in the plasma of the subject of about 947.92±20.24 (ng)(h)/ml following administration of three oral pharmaceutical compositions to a human.

6. The oral pharmaceutical composition according to claim 1, wherein it provides a urine elimination rate of the rifamycin SV in a subject to which the oral pharmaceutical composition is administered of not more than 1% of the total amount of rifamycin SV, or a pharmaceutically acceptable salt thereof, administered to the subject.

7. The oral pharmaceutical composition according to claim 1, wherein said pharmaceutical composition releases not more than 10% of the amount of rifamycin SV, or a pharmaceutically acceptable salt thereof, comprising the pharmaceutical composition when the pharmaceutical composition is placed in a USP dissolution apparatus II complying with USP <711> for 2 hours, wherein the dissolution apparatus comprises 1000 mL of an aqueous solution comprising 0.1 M hydrochloric acid and 0.4% macrogol cetostearyl ether at pH 1 and at a temperature of 37±0.5° C., and wherein the aqueous solution is stirred at a rate of 50 rpm.

8. The oral pharmaceutical composition according to claim 1, wherein the pharmaceutical composition contains no more than about 2 wt % of rifamycin S.

9. The oral pharmaceutical composition according claim 1, wherein the pharmaceutical composition contains no more than about 1 wt % of rifamycin B.

10. The oral pharmaceutical composition according to claim 1, wherein the pharmaceutical composition contains no more than 10,000 parts per million of ethanol.

11. The oral pharmaceutical composition according to claim 1, wherein the solid dosage form contains less than 2 wt % of rifamycin S and less than 1 wt % of rifamycin B following storage of the solid dosage form at 25° C. and 60% relative humidity for 3 months.

12. The oral pharmaceutical composition according to claim 1, wherein the solid dosage form is contained in a package, wherein the package comprises materials to protect the solid dosage form from heat and light.

13. The oral pharmaceutical composition according to claim 1, wherein the solid dosage form is in the form of a tablet.

14. A method of treating a condition in a subject in need thereof, comprising administering to the subject an effective amount of the oral pharmaceutical composition according to claim 1, wherein the condition is small intestine bacterial overgrowth (SIBO), irritable bowel syndrome (IBS), IBS having predominant diarrhea (IBS-D), IBS having alternated predominant diarrhea or constipation (IBS-M), or cholera.

15. The method according to claim 14, wherein the oral pharmaceutical composition is administered to the subject at a daily dose of 600 mg, 1200 mg or 1800 mg for a period from a few days up to several months.

16. A method of treating a subject suffering from IBS-D, comprising administering the oral pharmaceutical composition according to claim 1, wherein the oral pharmaceutical composition is administered to the subject three times per day for 1 or more days, and wherein the subject experiences a relief of stool consistency compared with a baseline according to a 7-point Bristol stool form scale.

17. The oral pharmaceutical composition according to claim 1, wherein the one or more hydrophilic compounds is selected from the group consisting of (i) cellulose derivative and their ester, or salt, (ii) alkylcelluloses, (iii) carboxyalkylcelluloses, (iv) polyvinyl alcohol, (v) carboxyvinyl derivative, (vi) polysaccharide, (v) natural or synthetic gum, (vi) alginic acid, and (vii) polyalcohol.

18. The oral pharmaceutical composition according to claim 1, wherein the one or more amphiphilic compounds (i) polar lipid, (ii) ceramide, (iii) glycol alkyl ether, and (iv) natural or synthetic gum.

* * * * *